United States Patent
Forsyth et al.

(10) Patent No.: US 11,974,822 B2
(45) Date of Patent: May 7, 2024

(54) METHOD FOR A SURVEILLANCE MARKER IN ROBOTIC-ASSISTED SURGERY

(71) Applicant: GLOBUS MEDICAL, INC., Audubon, PA (US)

(72) Inventors: Jeffrey Forsyth, Cranston, RI (US); Sanjay M. Joshi, Andover, MA (US); Neil R. Crawford, Chandler, AZ (US)

(73) Assignee: Globus Medical Inc., Audubon, PA (US)

(*) Notice: Subject to any disclaimer, the term of this patent is extended or adjusted under 35 U.S.C. 154(b) by 0 days.

(21) Appl. No.: 18/308,762

(22) Filed: Apr. 28, 2023

(65) Prior Publication Data

US 2023/0263581 A1    Aug. 24, 2023

Related U.S. Application Data

(63) Continuation of application No. 16/226,770, filed on Dec. 20, 2018, which is a continuation-in-part of application No. 15/448,670, filed on Mar. 3, 2017, now abandoned, which is a continuation-in-part of application No. 15/157,444, filed on May 18, 2016, which is a continuation-in-part of application No. 15/095,883, filed on Apr. 11, 2016, now Pat. No. 10,893,912, which is a continuation-in-part of application No. 14/062,707, filed on Oct. 24, 2013, (Continued)

(51) Int. Cl.
*A61B 34/20* (2016.01)
*A61B 34/30* (2016.01)
*A61B 90/00* (2016.01)

(52) U.S. Cl.
CPC .............. *A61B 34/20* (2016.02); *A61B 34/30* (2016.02); *A61B 2034/2057* (2016.02); *A61B 2034/2072* (2016.02); *A61B 2090/3916* (2016.02); *A61B 2090/3937* (2016.02); *A61B 2090/3991* (2016.02)

(58) Field of Classification Search
CPC . A61B 34/20; A61B 34/30; A61B 2034/2057; A61B 2034/2072; A61B 2090/3916; A61B 2090/3937
See application file for complete search history.

(56) References Cited

U.S. PATENT DOCUMENTS 4,150,293 A    4/1979    Franke
5,020,933 A    6/1991    Salvestro et al.
(Continued)

FOREIGN PATENT DOCUMENTS

AU    2015234609 A1    10/2016
CN        1536975 A    10/2004
(Continued)

OTHER PUBLICATIONS

US 8,231,638 B2, 07/2012, Swarup et al. (withdrawn)
(Continued)

*Primary Examiner* — Chao Sheng

(57) ABSTRACT

Devices, systems, and methods for providing a surveillance marker configured to detecting movement of a dynamic reference base attached to a patient a robot-assisted surgical procedure are provided. The surveillance marker and the dynamic reference base are connected to a bony structure independent of each other.

20 Claims, 18 Drawing Sheets

Related U.S. Application Data now Pat. No. 10,357,184, which is a continuation-in-part of application No. 13/924,505, filed on Jun. 21, 2013, now Pat. No. 9,782,229.

(60) Provisional application No. 62/608,188, filed on Dec. 20, 2017, provisional application No. 61/800,527, filed on Mar. 15, 2013, provisional application No. 61/662,702, filed on Jun. 21, 2012.

(56) References Cited

U.S. PATENT DOCUMENTS

| | | |
|---|---|---|
| 5,246,010 A | 9/1993 | Gazzara et al. |
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A * | 9/2000 | Cosman .............. A61B 34/20 606/130 |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,182,083 B2 | 2/2007 | Yanof et al. |
| 7,194,120 B2 | 3/2007 | Wicker et al. |
| 7,197,107 B2 | 3/2007 | Arai et al. |
| 7,207,995 B1 | 4/2007 | Vandewalle |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |

(56) References Cited

U.S. PATENT DOCUMENTS

| | | |
|---|---|---|
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jenser |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,313,430 B1 | 11/2012 | Pimenta |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |

(56) References Cited

U.S. PATENT DOCUMENTS

| | | |
|---|---|---|
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,463,073 B2 | 10/2016 | Gill et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |

(56) References Cited

U.S. PATENT DOCUMENTS

| | | |
|---|---|---|
| 10,034,717 B2 | 7/2018 | Miller et al. |
| 10,575,906 B2 | 3/2020 | Wu |
| 2001/0036302 A1 | 11/2001 | Miller |
| 2002/0035321 A1 | 3/2002 | Bucholz et al. |
| 2003/0125622 A1 | 7/2003 | Schweikard et al. |
| 2003/0161442 A1 | 8/2003 | Zeiss |
| 2004/0024311 A1 | 2/2004 | Quaid |
| 2004/0034302 A1 | 2/2004 | Abovitz et al. |
| 2004/0068172 A1 | 4/2004 | Nowinski et al. |
| 2004/0076259 A1 | 4/2004 | Jensen et al. |
| 2004/0097952 A1 | 5/2004 | Sarin et al. |
| 2004/0153191 A1 | 8/2004 | Grimm et al. |
| 2004/0157188 A1 | 8/2004 | Luth et al. |
| 2004/0215071 A1 | 10/2004 | Frank et al. |
| 2005/0085714 A1 | 4/2005 | Foley et al. |
| 2005/0096502 A1 | 5/2005 | Khalili |
| 2005/0107679 A1 | 5/2005 | Geiger et al. |
| 2005/0143651 A1 | 6/2005 | Verard et al. |
| 2005/0149045 A1 | 7/2005 | Elliott |
| 2005/0171558 A1 | 8/2005 | Abovitz et al. |
| 2005/0215888 A1 | 9/2005 | Grimm et al. |
| 2006/0036264 A1 | 2/2006 | Selover et al. |
| 2006/0100610 A1 | 5/2006 | Wallace et al. |
| 2006/0142657 A1 | 6/2006 | Quaid et al. |
| 2006/0173329 A1 | 8/2006 | Marquart et al. |
| 2006/0178559 A1 | 8/2006 | Kumar et al. |
| 2006/0184396 A1 | 8/2006 | Dennis et al. |
| 2006/0241416 A1 | 10/2006 | Marquart et al. |
| 2006/0264963 A1 | 11/2006 | Reed et al. |
| 2006/0291612 A1 | 12/2006 | Nishide et al. |
| 2007/0001879 A1 | 1/2007 | Kaftan et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0078475 A1 | 4/2007 | Bodduluri et al. |
| 2007/0122020 A1 | 5/2007 | Claus et al. |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2007/0238985 A1 | 10/2007 | Smith et al. |
| 2008/0004523 A1 | 1/2008 | Jensen |
| 2008/0010706 A1 | 1/2008 | Moses et al. |
| 2008/0013809 A1* | 1/2008 | Zhu .................... G16H 20/40 382/128 |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0119725 A1 | 5/2008 | Loyd |
| 2008/0144906 A1 | 6/2008 | Allred et al. |
| 2008/0154389 A1 | 6/2008 | Smith et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0188934 A1 | 8/2008 | Moser et al. |
| 2008/0200794 A1 | 8/2008 | Teichman et al. |
| 2008/0214922 A1 | 9/2008 | Hartmann et al. |
| 2008/0228068 A1 | 9/2008 | Viswanathan et al. |
| 2008/0228195 A1 | 9/2008 | von Jako et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0099445 A1 | 4/2009 | Burger |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0234217 A1 | 9/2009 | Mire et al. |
| 2009/0240141 A1 | 9/2009 | Neubauer et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2009/0306480 A1 | 12/2009 | Protopsaltis |
| 2009/0306499 A1 | 12/2009 | Van Vorhis et al. |
| 2010/0022874 A1 | 1/2010 | Wang et al. |
| 2010/0039506 A1 | 2/2010 | Sarvestani et al. |
| 2010/0046718 A1 | 2/2010 | Weiser et al. |
| 2010/0076305 A1 | 3/2010 | Maier-Hein et al. |
| 2010/0114288 A1 | 5/2010 | Haller et al. |
| 2010/0125286 A1 | 5/2010 | Wang et al. |
| 2010/0130986 A1 | 5/2010 | Mailloux et al. |
| 2010/0174410 A1 | 7/2010 | Greer et al. |
| 2010/0228117 A1 | 9/2010 | Hartmann |
| 2010/0228265 A1 | 9/2010 | Prisco |
| 2010/0228340 A1 | 9/2010 | Erbel et al. |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0019884 A1 | 1/2011 | Blau |
| 2011/0020084 A1 | 1/2011 | Brett et al. |
| 2011/0022229 A1 | 1/2011 | Jang et al. |
| 2011/0040305 A1 | 2/2011 | Gomez et al. |
| 2011/0071347 A1 | 3/2011 | Rogers et al. |
| 2011/0077504 A1 | 3/2011 | Fischer et al. |
| 2011/0082468 A1 | 4/2011 | Hagag et al. |
| 2011/0098553 A1 | 4/2011 | Robbins et al. |
| 2011/0137152 A1 | 6/2011 | Li |
| 2011/0184245 A1 | 7/2011 | Xia et al. |
| 2011/0190588 A1 | 8/2011 | McKay |
| 2011/0213379 A1 | 9/2011 | Blau et al. |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0257653 A1 | 10/2011 | Hughes et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Solsona et al. |
| 2011/0295370 A1 | 12/2011 | Suh et al. |
| 2011/0306873 A1 | 12/2011 | Shenai et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0289820 A1 | 11/2012 | Rohling |
| 2012/0294498 A1 | 11/2012 | Popovic |
| 2012/0296203 A1 | 11/2012 | Hartmann et al. |

(56) References Cited

U.S. PATENT DOCUMENTS

| | | |
|---|---|---|
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0051647 A1 | 2/2013 | Miao et al. |
| 2013/0060146 A1 | 3/2013 | Yang et al. |
| 2013/0060337 A1 | 3/2013 | Petersheim et al. |
| 2013/0064427 A1 | 3/2013 | Picard et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0165948 A1 | 6/2013 | Popovic |
| 2013/0178867 A1 | 7/2013 | Farritor et al. |
| 2013/0178868 A1 | 7/2013 | Roh |
| 2013/0178870 A1 | 7/2013 | Schena |
| 2013/0184873 A1 | 7/2013 | Namiki |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0268007 A1 | 10/2013 | Rezach et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0279784 A1 | 10/2013 | Gill et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325029 A1 | 12/2013 | Hourtash et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345718 A1 | 12/2013 | Crawford et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0052150 A1 | 2/2014 | Taylor et al. |
| 2014/0058406 A1 | 2/2014 | Tsekos |
| 2014/0067343 A1 | 3/2014 | Yamagata |
| 2014/0073914 A1 | 3/2014 | Avallee et al. |
| 2014/0080086 A1 | 3/2014 | Chen |
| 2014/0081128 A1 | 3/2014 | Verard et al. |
| 2014/0088410 A1 | 3/2014 | Wu |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135744 A1 | 5/2014 | Stein et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0200587 A1 | 7/2014 | Pompee et al. |
| 2014/0130810 A1 | 8/2014 | Azizian et al. |
| 2014/0221819 A1 | 8/2014 | Sarment |
| 2014/0221822 A1 | 8/2014 | Ehlers et al. |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275955 A1 | 9/2014 | Crawford et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276943 A1 | 9/2014 | Bowling et al. |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0336669 A1 | 11/2014 | Park |
| 2014/0343416 A1 | 11/2014 | Panescu et al. |
| 2014/0357989 A1 | 12/2014 | Hendriks et al. |
| 2014/0364720 A1 | 12/2014 | Darrow et al. |
| 2014/0371577 A1 | 12/2014 | Maillet et al. |
| 2015/0032164 A1 | 1/2015 | Crawford et al. |
| 2015/0039034 A1 | 2/2015 | Frankel et al. |
| 2015/0049174 A1 | 2/2015 | Lee et al. |
| 2015/0085970 A1 | 3/2015 | Bouhnik et al. |
| 2015/0100066 A1 | 4/2015 | Kostrzewski et al. |
| 2015/0100067 A1 | 4/2015 | Cavanagh et al. |
| 2015/0146847 A1 | 5/2015 | Liu |
| 2015/0150524 A1 | 6/2015 | Yorkston et al. |
| 2015/0157416 A1 | 6/2015 | Andersson |
| 2015/0157468 A1 | 6/2015 | Wakayama et al. |
| 2015/0196261 A1 | 7/2015 | Funk |
| 2015/0196365 A1 | 7/2015 | Kostrzewski et al. |
| 2015/0209056 A1 | 7/2015 | Shoham et al. |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0030129 A1 | 2/2016 | Christian et al. |
| 2016/0033284 A1 | 2/2016 | Sato |
| 2016/0063707 A1 | 3/2016 | Masumoto |
| 2016/0166329 A1 | 6/2016 | Langan et al. |
| 2016/0220320 A1 | 8/2016 | Crawford et al. |
| 2016/0235480 A1 | 8/2016 | Scholl et al. |
| 2016/0235492 A1 | 8/2016 | Morard et al. |
| 2016/0235493 A1 | 8/2016 | Leboeuf, II et al. |
| 2016/0249990 A1 | 9/2016 | Glozman et al. |
| 2016/0256225 A1 | 9/2016 | Crawford et al. |
| 2016/0296266 A1 | 10/2016 | Chandanson et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0000562 A1 | 1/2017 | Frank et al. |
| 2017/0007327 A1 | 1/2017 | Haider et al. |
| 2017/0020609 A1 | 1/2017 | Wentorf et al. |
| 2017/0079727 A1 | 3/2017 | Crawford et al. |

(56) References Cited

U.S. PATENT DOCUMENTS

| | | | |
|---|---|---|---|
| 2017/0112552 A1 | 4/2017 | Sinnott et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0189126 A1 | 7/2017 | Weir |
| 2017/0202629 A1 | 7/2017 | Maillet et al. |
| 2017/0209222 A1 | 7/2017 | Gassner et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0245946 A1 | 8/2017 | Tabandeh et al. |
| 2017/0245951 A1 | 8/2017 | Crawford et al. |
| 2017/0258426 A1 | 9/2017 | Risher-Kelly et al. |
| 2017/0258526 A1 | 9/2017 | Lang |
| 2017/0258532 A1 | 9/2017 | Shalayev et al. |
| 2017/0258535 A1 | 9/2017 | Crawford et al. |
| 2017/0265952 A1 | 9/2017 | Donhowe et al. |
| 2017/0273748 A1 | 9/2017 | Hourtash et al. |
| 2017/0296277 A1 | 10/2017 | Hourtash et al. |
| 2017/0312032 A1 | 11/2017 | Amanatullah et al. |
| 2017/0333137 A1 | 11/2017 | Roessler |
| 2017/0348061 A1 | 12/2017 | Joshi et al. |
| 2017/0360493 A1 | 12/2017 | Zucher et al. |
| 2018/0008355 A1 | 1/2018 | Mozes et al. |
| 2018/0049825 A1 | 2/2018 | Kwon et al. |
| 2018/0064496 A1 | 3/2018 | Hladio et al. |
| 2018/0064497 A1 | 3/2018 | Hussain et al. |
| 2018/0066794 A1 | 3/2018 | Okuda et al. |
| 2018/0092699 A1 | 4/2018 | Finley |
| 2018/0200016 A1 | 7/2018 | Chappuis |
| 2018/0249981 A1 | 9/2018 | Johnson et al. |
| 2018/0325608 A1 | 11/2018 | Kang et al. |
| 2018/0325610 A1 | 11/2018 | Cameron et al. |

FOREIGN PATENT DOCUMENTS

| | | |
|---|---|---|
| CN | 1714742 A | 1/2006 |
| CN | 102036615 A | 4/2011 |
| CN | 202027725 U | 11/2011 |
| CN | 102438551 A | 5/2012 |
| CN | 102596062 A | 7/2012 |
| CN | 102612350 A | 7/2012 |
| CN | 102933163 A | 2/2013 |
| CN | 104334110 A | 2/2015 |
| CN | 104994805 A | 10/2015 |
| CN | 105101903 A | 11/2015 |
| CN | 105939687 A | 9/2016 |
| CN | 106163446 A | 11/2016 |
| CN | 106691600 A | 5/2017 |
| CN | 106999168 A | 8/2017 |
| CN | 106999245 A | 8/2017 |
| CN | 107088091 A | 8/2017 |
| CN | 107405170 A | 11/2017 |
| CN | 107545585 A | 1/2018 |
| CN | 108652743 B | 10/2018 |
| CN | 209153975 U | 7/2019 |
| CN | 107847275 B | 10/2020 |
| DE | 102013012840 A1 | 2/2015 |
| DE | 102014221469 A1 | 4/2016 |
| DE | 102012215001 B4 | 12/2021 |
| EP | 1103223 A2 | 5/2001 |
| EP | 1224918 A2 | 7/2002 |
| EP | 1346687 A1 | 9/2003 |
| EP | 1523950 A1 | 4/2005 |
| EP | 2468207 A1 | 6/2012 |
| EP | 2471483 A1 | 7/2012 |
| EP | 2471617 A1 | 7/2012 |
| EP | 3181085 A1 | 6/2017 |
| EP | 3391848 A2 | 10/2018 |
| EP | 3517069 A1 | 7/2019 |
| JP | 11-313837 A | 11/1999 |
| JP | 2001135734 A | 5/2001 |
| JP | 2002253574 A | 9/2002 |
| JP | 2004518475 A | 6/2004 |
| JP | 2007-044488 A | 2/2007 |
| JP | 2007-531543 A | 11/2007 |
| JP | 2007534351 A | 11/2007 |
| JP | 2007537835 A | 12/2007 |
| JP | 2008507361 A | 3/2008 |
| JP | 2008188417 A | 8/2008 |
| JP | 2008-538184 A | 10/2008 |
| JP | 2009537229 A | 10/2009 |
| JP | 2011-120782 A | 6/2011 |
| JP | 2012075507 A | 4/2012 |
| JP | 2013075195 A | 4/2013 |
| JP | 2013-541365 A | 11/2013 |
| JP | 2014036700 A | 2/2014 |
| JP | 2014-48228 A | 3/2014 |
| JP | 2014097220 A | 5/2014 |
| JP | 2015-504721 A | 2/2015 |
| JP | 201536161 A | 2/2015 |
| JP | 2015100677 A | 6/2015 |
| JP | 2015521084 A | 7/2015 |
| JP | 2015528713 A | 10/2015 |
| JP | 2015-534480 A | 12/2015 |
| JP | 2016-33474 A | 3/2016 |
| JP | 2016043211 A | 4/2016 |
| JP | 2016185225 A | 10/2016 |
| JP | 2016-193222 A | 11/2016 |
| JP | 2016193222 A | 11/2016 |
| JP | 2017087313 A | 5/2017 |
| JP | 2017-528255 A | 9/2017 |
| JP | 2017176848 A | 10/2017 |
| JP | 2017530842 A | 10/2017 |
| JP | 2017223657 A | 12/2017 |
| JP | 2018011938 A | 1/2018 |
| JP | 2018-027288 A | 2/2018 |
| JP | 2018516107 A | 6/2018 |
| JP | 2018-114283 A | 7/2018 |
| JP | 2018523516 A | 8/2018 |
| JP | 2018-202156 A | 12/2018 |
| JP | 2021-25802 A | 2/2021 |
| JP | 2021025802 A | 2/2021 |
| WO | 03007198 A2 | 1/2003 |
| WO | 2005039417 A1 | 5/2005 |
| WO | 2009092164 A1 | 7/2009 |
| WO | 2009126953 A2 | 10/2009 |
| WO | 2011128766 A2 | 10/2011 |
| WO | 2012050634 A1 | 4/2012 |
| WO | 2013114823 A1 | 8/2013 |
| WO | 2013118047 A1 | 8/2013 |
| WO | 2013192598 A1 | 12/2013 |
| WO | 2014010760 A1 | 1/2014 |
| WO | 2014062890 A1 | 4/2014 |
| WO | 2014139023 A1 | 9/2014 |
| WO | 2015023665 A1 | 2/2015 |
| WO | 2015052718 A1 | 4/2015 |
| WO | 2015079775 A1 | 6/2015 |
| WO | 2015142762 A1 | 9/2015 |
| WO | 201613049 A1 | 1/2016 |
| WO | 2016087539 A2 | 6/2016 |
| WO | 2016114834 A2 | 7/2016 |
| WO | 2016154557 A1 | 9/2016 |
| WO | 2016170372 A1 | 10/2016 |
| WO | 2017147596 A1 | 8/2017 |
| WO | 2017/169098 A1 | 10/2017 |
| WO | 2017186799 A1 | 11/2017 |
| WO | 2017204832 A1 | 11/2017 |
| WO | 2017221257 A1 | 12/2017 |
| WO | 2018075784 A1 | 4/2018 |
| WO | 2018165767 A1 | 9/2018 |
| WO | 2018183461 A1 | 10/2018 |

OTHER PUBLICATIONS

Marintschev et al.: "Navigation of vertebro-pelvic fixations based on CT-fluoro macthing", European Spine Journal, Springer, Berlin, DE, vol. 19, No. 11, pp. 1921-1927, Jun. 16, 2010.

Andreas Alk et al: "Smart Device Assisted Method for Rod Length and Rod Radius Measurement in Percutaneous Pedicle Screw

(56) References Cited

OTHER PUBLICATIONS

Surgery", Przeglad Elektrotechniczny, vol. 3, Mar. 5, 2016 (Mar. 5, 2016), pp. 30-33, XP055668769, PO ISSN: 0033-2097, DOI: 10.15199/48.2016.03.07.

Alk et al., "Smart Device Assisted Method for Rod Length and Rod Radius Measurement in Percutaneious Pedicle Screw Surgery", Prizeglad Elektrotechniczny, vol. 3, Mar. 5, 2016, pp. 30-33.

Markelj et al.: "A review of 3D/2D registration methods for image-guided interventions", Medical Image Analysis, Oxford University Press, Oxford, GB, vol. 16, No. 3, pp. 642-661, Apr. 1, 2012.

Gong Ren Hui et al.: "Interactive initialization of 2D/3D rigid registration", Medical Physics, AIP, Melville, NY, US, vol. 40, No. 12, 14 pages, Dec. 2013.

Dumenil A et al.: "A versatile intensity-based 3D/2D rigid registration compatible with mobile C-arm for endovascular treatment of abdominal aortic aneurysm", International Journal of Computer Assisted Radiology and Surgery, Springer, DE, vol. 11, No. 9, pp. 1713-1729, May 26, 2016.

\* cited by examiner

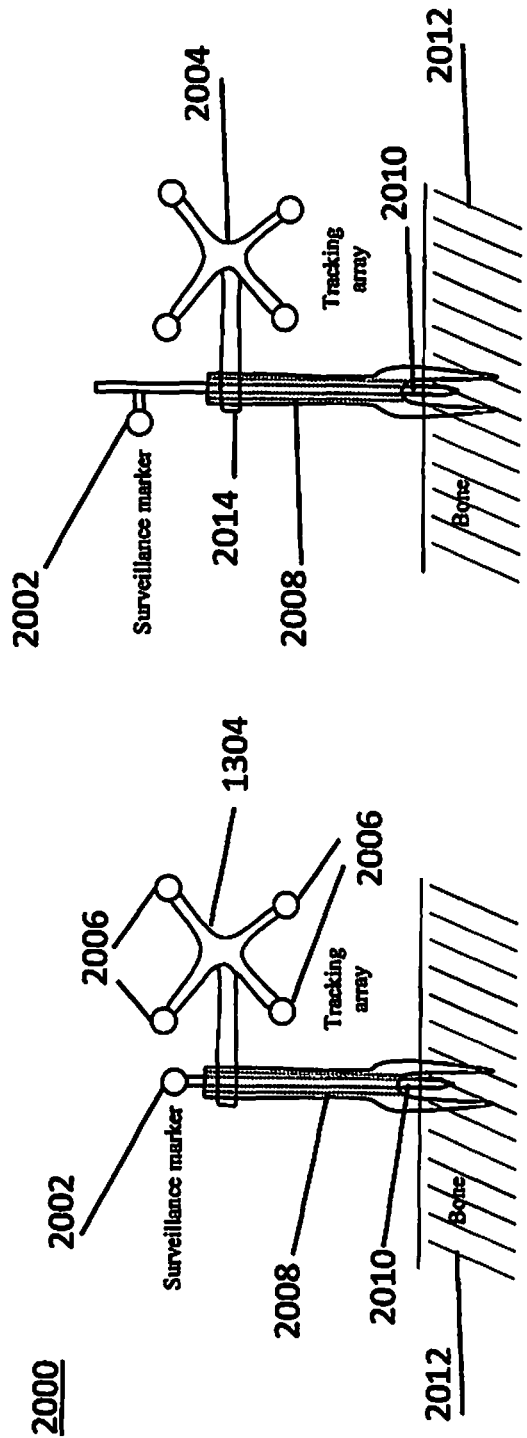

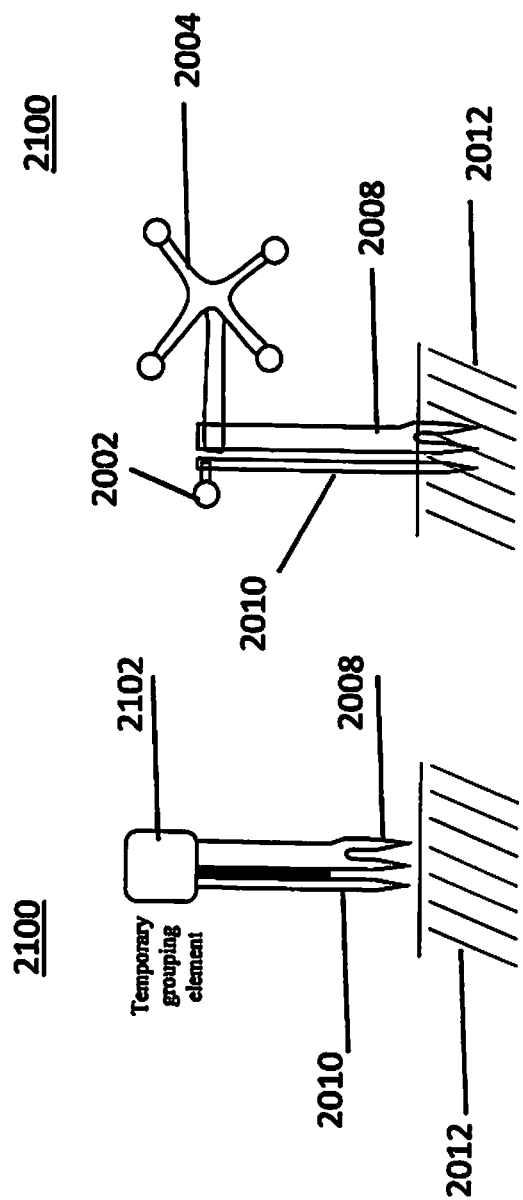

METHOD FOR A SURVEILLANCE MARKER IN ROBOTIC-ASSISTED SURGERY

CROSS-REFERENCE TO RELATED APPLICATIONS

This application is a continuation of U.S. patent application Ser. No. 16/226,770, filed on Dec. 20, 2018, which i) claims priority to Provisional Patent Application Ser. No. 62/608,188 filed on Dec. 20, 2017, and ii) is a continuation-in-part of U.S. patent application Ser. No. 15/448,670 filed on Mar. 3, 2017, which is a continuation-in-part of U.S. patent application Ser. No. 15/157,444 filed May 18, 2016, which is a continuation-in-part application of U.S. patent application Ser. No. 15/095,883 filed on Apr. 11, 2016 (published as U.S. Patent Publication No. 2016/0220320 A1), which is a continuation-in-part application of U.S. patent application Ser. No. 14/062,707 filed on Oct. 24, 2013 (published as U.S. Patent Publication No. 2014/0275955 A1), which is a continuation-in-part application of U.S. patent application Ser. No. 13/924,505 filed on Jun. 21, 2013 (published as U.S. Patent Publication No. 2013/0345718 A1, with corrected publication as U.S. Patent Publication No. 2016/0242849 A9), which is a nonprovisional patent application that claims priority to U.S. provisional patent application No. 61/662,702 filed on Jun. 21, 2012, and claims priority to U.S. provisional patent application No. 61/800,527 filed on Mar. 15, 2013, the entire contents of all of which are incorporated herein by reference.

FIELD OF THE INVENTION

The present disclosure relates to surveillance marker implementation for robot-assisted surgical techniques.

BACKGROUND OF THE INVENTION

Various medical procedures require the accurate localization of a three-dimensional position of a surgical instrument within the body in order to effect optimized treatment. For example, some surgical procedures to fuse vertebrae require that a surgeon drill multiple holes into the bone structure at specific locations. To achieve high levels of mechanical integrity in the fusing system, and to balance the forces created in the bone structure, it is necessary that the holes are drilled at the correct location. Vertebrae, like most bone structures, have complex shapes including non-planar curved surfaces making accurate and perpendicular drilling difficult.

Conventionally, using currently-available systems and methods, a surgeon manually holds and positions a drill guide tube by using a guidance system to overlay the drill tube's position onto a three dimensional image of the anatomical structures of a patient, for example, bone structures of the patient. This manual process is both tedious, time consuming, and error-prone. Further, whether the surgery can be considered successful largely depends upon the dexterity of the surgeon who performs it. Thus, there is a need for the use of robot assisted surgery to more accurately position surgical instruments and more accurately depict the position of those instruments in relation to the anatomical structures of the patient.

Currently, limited robotic assistance for surgical procedures is available. For example, certain systems allow a user to control a robotic actuator. These systems convert a surgeon's gross movements into micro-movements of the robotic actuator to more accurately position and steady the surgical instruments when undergoing surgery. Although these systems may aid in eliminating hand tremor and provide the surgeon with improved ability to work through a small opening, like many of the robots commercially available today, these systems are expensive, obtrusive, and require a cumbersome setup for the robot in relation to the patient and the user (e.g., a surgeon).

In some robotic-assisted systems, registration techniques may be used in order to properly track surgical instruments in relation to 2D and/or 3D images of the patient's target anatomy. As previously discussed in parent applications to the present disclosure (listed above), a dynamic reference base (DRB) may be physically attached to bony structures of a patient. After registration of the markers to images of the patient's anatomy, the DRB may be used as a reference point in order to properly display the position of navigated surgical instruments in relation to images of the patient's anatomy. In the event the DRB is shifted or dislodged, the registration process may need to be reinitiated so ensure proper registration and that the visual display of the navigated instruments relative to images of the patient's anatomy are accurate to real-life movements of the instruments.

One way to determine if the DRB has been dislodged or move is through the use of a surveillance maker. The use of surveillance makers has been previously described in U.S. patent application Ser. No. 13/294,505 the contents of which are incorporated herein by reference. The surveillance marker is a single tracked marker attached to the patient in a location other than the location of the DRB that tracks patient position. If the patient is moved relative to the tracking cameras, the surveillance marker and DRB would be expected to move together by the same amount, with no relative movement between DRB and surveillance marker. However, movement of the surveillance marker relative to tracking markers on the DRB is an indicator that the DRB may have been accidentally dislodged.

The surveillance marker may require additional preparation and surgical incision of the patient at the location where the surveillance marker is to be applied. Thus, there is a need to allow a surgeon to attach the surveillance marker to the patient using the same incision as was used for DRB placement. To improve functionality, the surveillance marker may not rigidly interface with the DRB.

Accordingly, there exists a need for a surveillance marker that does not rigidly interface with the DRB while still effectively detecting DRB dislodgment. This may be accomplished by the present disclosure by attaching the surveillance marker to bone near the DRB. For example, having the surveillance marker on a post that does not touch the DRB.

SUMMARY OF THE INVENTION

To meet this and other needs, devices, systems, and methods for detecting the presence of unintended movement of a surgical instrument during a surgical procedure are provided.

According to one exemplary embodiment, the present disclosure provides a system for checking accuracy of registration of a patient to a surgical robot. The system includes a dynamic reference base including at least one array marker, a dynamic reference base post connected to the dynamic reference base, a surveillance marker disposed at a predetermined distance from the dynamic reference base; and a surveillance marker post connected to the surveillance marker and disposed independent of the dynamic reference base post. The surveillance marker post and the dynamic reference base are attached to different portions of a bony structure.

According to another exemplary embodiment, the present disclosure provides a system for accuracy of registration of a patient to a surgical robot. The system comprising a dynamic reference base including at least one array marker, a dynamic reference base post associated with the dynamic reference base, a surveillance marker disposed at a predetermined distance from the dynamic reference base, a surveillance marker post associated with the surveillance marker; and a temporary grouping element configured to receive the surveillance marker post and the dynamic reference base post. The surveillance marker post and the dynamic reference base are attached to different portions of a bony structure while received in the temporary grouping element. The temporary grouping member may be configured to be removed from the surveillance marker post and dynamic reference base post after attachment to the bony structure.

BRIEF DESCRIPTION OF THE DRAWINGS

The invention and the following detailed description of certain embodiments thereof may be understood by reference to the following figures:

FIGS. 13A-13B illustrate a surveillance marker in accordance with exemplary embodiments of the present disclosure;

FIGS. 14A-14B illustrate a surveillance marker in accordance with exemplary embodiments of the present disclosure.

DETAILED DESCRIPTION OF THE INVENTION

Figure 1:
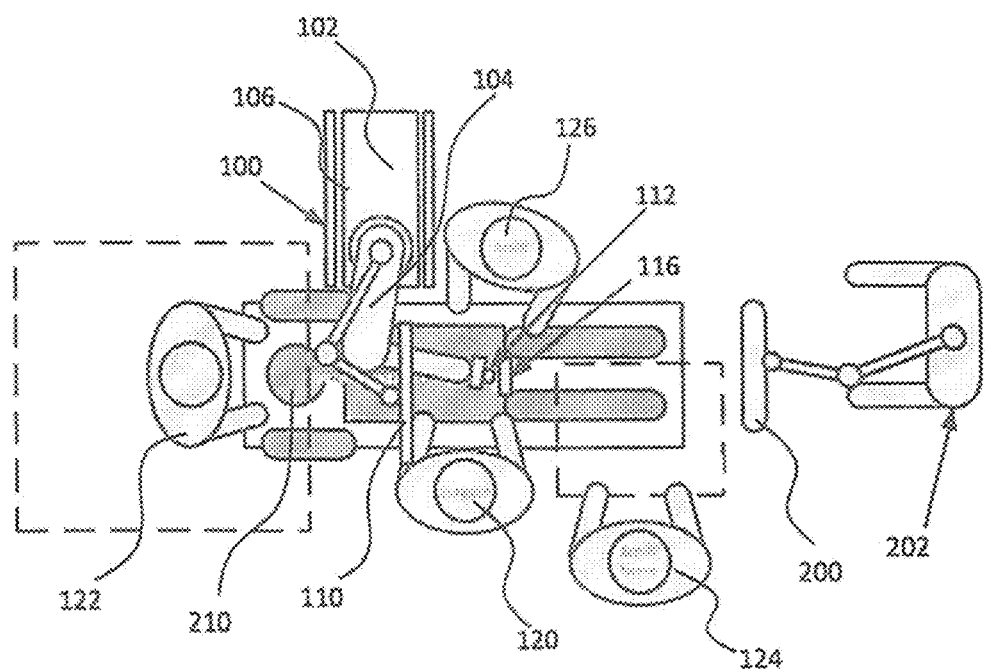
FIG. 1 is an overhead view of a potential arrangement for locations of the robotic system, patient, surgeon, and other medical personnel during a surgical procedure.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Figure 2:
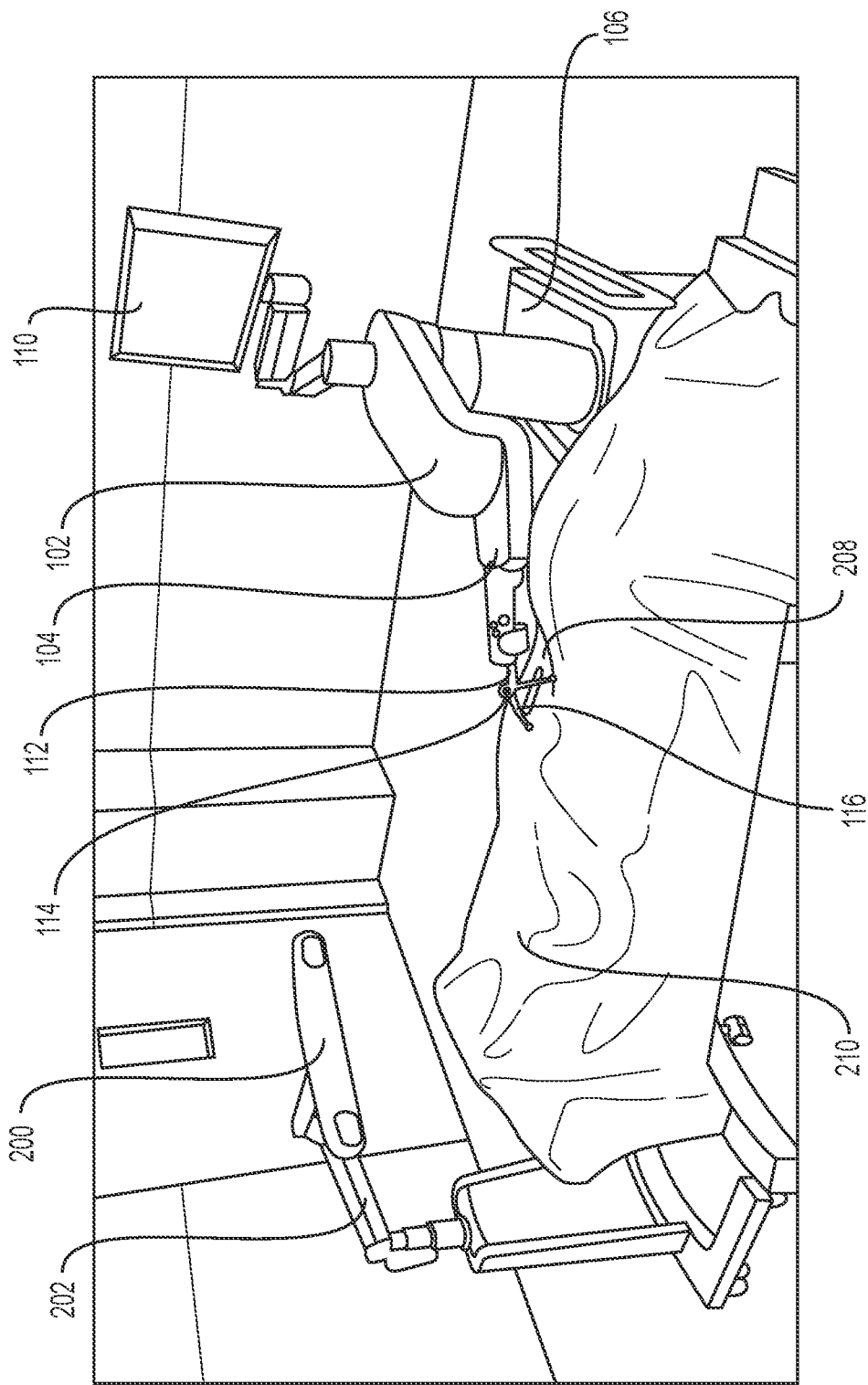
FIG. 2 illustrates the robotic system including positioning of the surgical robot and the camera relative to the patient according to one embodiment.

Turning now to the drawing, FIGS. 1 and 2 illustrate a surgical robot system 100 in accordance with an exemplary embodiment. Surgical robot system 100 may include, for example, a surgical robot 102, one or more robot arms 104, a base 106, a display 110, an end effector 112, for example, including a guide tube 114, and one or more tracking markers 118. The surgical robot system 100 may include a patient tracking device 116 also including one or more tracking markers 118, which is adapted to be secured directly to the patient 210 (e.g., to the bone of the patient 210). The surgical robot system 100 may also utilize a camera 200, for example, positioned on a camera stand 202. The camera stand 202 can have any suitable configuration to move, orient, and support the camera 200 in a desired position. The camera 200 may include any suitable camera or cameras, such as one or more infrared cameras (e.g., bifocal or stereophotogrammetric cameras), able to identify, for example, active and passive tracking markers 118 in a given measurement volume viewable from the perspective of the camera 200. The camera 200 may scan the given measurement volume and detect the light that comes from the markers 118 in order to identify and determine the position of the markers 118 in three dimensions. For example, active markers 118 may include infrared-emitting markers that are activated by an electrical signal (e.g., infrared light emitting diodes (LEDs)), and passive markers 118 may include retro-reflective markers that reflect infrared light (e.g., they reflect incoming IR radiation into the direction of the incoming light), for example, emitted by illuminators on the camera 200 or other suitable device.

FIGS. 1 and 2 illustrate a potential configuration for the placement of the surgical robot system 100 in an operating room environment. For example, the robot 102 may be positioned near or next to patient 210. Although depicted near the head of the patient 210, it will be appreciated that the robot 102 can be positioned at any suitable location near the patient 210 depending on the area of the patient 210 undergoing the operation. The camera 200 may be separated from the robot system 100 and positioned at the foot of patient 210. This location allows the camera 200 to have a direct visual line of sight to the surgical field 208. Again, it is contemplated that the camera 200 may be located at any suitable position having line of sight to the surgical field 208. In the configuration shown, the surgeon 120 may be positioned across from the robot 102, but is still able to manipulate the end effector 112 and the display 110. A surgical assistant 126 may be positioned across from the surgeon 120 again with access to both the end effector 112 and the display 110. If desired, the locations of the surgeon 120 and the assistant 126 may be reversed. The traditional areas for the anesthesiologist 122 and the nurse or scrub tech 124 remain unimpeded by the locations of the robot 102 and camera 200.

With respect to the other components of the robot 102, the display 110 can be attached to the surgical robot 102 and in other exemplary embodiments, display 110 can be detached from surgical robot 102, either within a surgical room with the surgical robot 102, or in a remote location. End effector 112 may be coupled to the robot arm 104 and controlled by at least one motor. In exemplary embodiments, end effector 112 can comprise a guide tube 114, which is able to receive and orient a surgical instrument 608 (described further herein) used to perform surgery on the patient 210. As used herein, the term "end effector" is used interchangeably with the terms "end-effectuator" and "effectuator element." Although generally shown with a guide tube 114, it will be appreciated that the end effector 112 may be replaced with any suitable instrumentation suitable for use in surgery. In some embodiments, end effector 112 can comprise any known structure for effecting the movement of the surgical instrument 608 in a desired manner.

The surgical robot 102 is able to control the translation and orientation of the end effector 112. The robot 102 is able to move end effector 112 along x-, y-, and z-axes, for example. The end effector 112 can be configured for selective rotation about one or more of the x-, y-, and z-axis, and a Z Frame axis (such that one or more of the Euler Angles (e.g., roll, pitch, and/or yaw) associated with end effector 112 can be selectively controlled). In some exemplary embodiments, selective control of the translation and orientation of end effector 112 can permit performance of medical procedures with significantly improved accuracy compared to conventional robots that utilize, for example, a six degree of freedom robot arm comprising only rotational axes. For example, the surgical robot system 100 may be used to operate on patient 210, and robot arm 104 can be positioned above the body of patient 210, with end effector 112 selectively angled relative to the z-axis toward the body of patient 210.

In some exemplary embodiments, the position of the surgical instrument 608 can be dynamically updated so that surgical robot 102 can be aware of the location of the surgical instrument 608 at all times during the procedure. Consequently, in some exemplary embodiments, surgical robot 102 can move the surgical instrument 608 to the desired position quickly without any further assistance from a physician (unless the physician so desires). In some further embodiments, surgical robot 102 can be configured to correct the path of the surgical instrument 608 if the surgical instrument 608 strays from the selected, preplanned trajectory. In some exemplary embodiments, surgical robot 102 can be configured to permit stoppage, modification, and/or manual control of the movement of end effector 112 and/or the surgical instrument 608. Thus, in use, in exemplary embodiments, a physician or other user can operate the system 100, and has the option to stop, modify, or manually control the autonomous movement of end effector 112 and/or the surgical instrument 608. Further details of surgical robot system 100 including the control and movement of a surgical instrument 608 by surgical robot 102 can be found in co-pending U.S. patent application Ser. No. 13/924,505, which is incorporated herein by reference in its entirety.

The robotic surgical system 100 can comprise one or more tracking markers 118 configured to track the movement of robot arm 104, end effector 112, patient 210, and/or the surgical instrument 608 in three dimensions. In exemplary embodiments, a plurality of tracking markers 118 can be mounted (or otherwise secured) thereon to an outer surface of the robot 102, such as, for example and without limitation, on base 106 of robot 102, on robot arm 104, or on the end effector 112. In exemplary embodiments, at least one tracking marker 118 of the plurality of tracking markers 118 can be mounted or otherwise secured to the end effector 112. One or more tracking markers 118 can further be mounted (or otherwise secured) to the patient 210. In exemplary embodiments, the plurality of tracking markers 118 can be positioned on the patient 210 spaced apart from the surgical field 208 to reduce the likelihood of being obscured by the surgeon, surgical tools, or other parts of the robot 102. Further, one or more tracking markers 118 can be further mounted (or otherwise secured) to the surgical tools 608 (e.g., a screw driver, dilator, implant inserter, or the like). Thus, the tracking markers 118 enable each of the marked objects (e.g., the end effector 112, the patient 210, and the surgical tools 608) to be tracked by the robot 102. In exemplary embodiments, system 100 can use tracking information collected from each of the marked objects to calculate the orientation and location, for example, of the end effector 112, the surgical instrument 608 (e.g., positioned in the tube 114 of the end effector 112), and the relative position of the patient 210.

In exemplary embodiments, one or more of markers 118 may be optical markers. In some embodiments, the positioning of one or more tracking markers 118 on end effector 112 can maximize the accuracy of the positional measurements by serving to check or verify the position of end effector 112. Further details of surgical robot system 100 including the control, movement and tracking of surgical robot 102 and of a surgical instrument 608 can be found in co-pending U.S. patent application Ser. No. 13/924,505, which is incorporated herein by reference in its entirety.

Exemplary embodiments include one or more markers 118 coupled to the surgical instrument 608. In exemplary embodiments, these markers 118, for example, coupled to the patient 210 and surgical instruments 608, as well as markers 118 coupled to the end effector 112 of the robot 102 can comprise conventional infrared light-emitting diodes (LEDs) or an Optotrak® diode capable of being tracked using a commercially available infrared optical tracking system such as Optotrak®. Optotrak® is a registered trademark of Northern Digital Inc., Waterloo, Ontario, Canada. In other embodiments, markers 118 can comprise conventional reflective spheres capable of being tracked using a commercially available optical tracking system such as Polaris Spectra. Polaris Spectra is also a registered trademark of Northern Digital, Inc. In an exemplary embodiment, the markers 118 coupled to the end effector 112 are active markers which comprise infrared light-emitting diodes which may be turned on and off, and the markers 118 coupled to the patient 210 and the surgical instruments 608 comprise passive reflective spheres.

In exemplary embodiments, light emitted from and/or reflected by markers 118 can be detected by camera 200 and can be used to monitor the location and movement of the marked objects. In alternative embodiments, markers 118 can comprise a radio-frequency and/or electromagnetic reflector or transceiver and the camera 200 can include or be replaced by a radio-frequency and/or electromagnetic transceiver.

Figure 3:
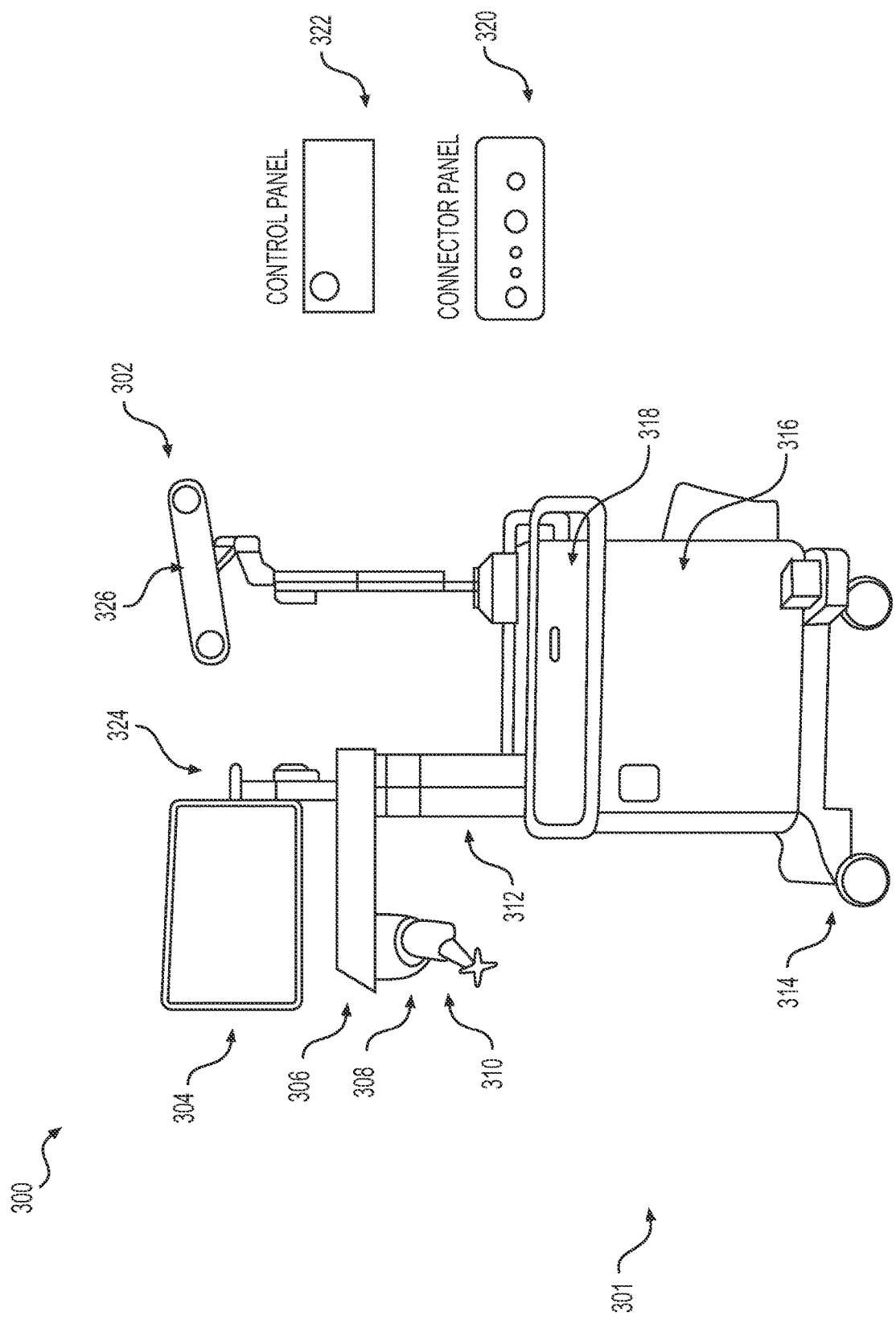
FIG. 3 illustrates a surgical robotic system in accordance with an exemplary embodiment.
Figure 4:
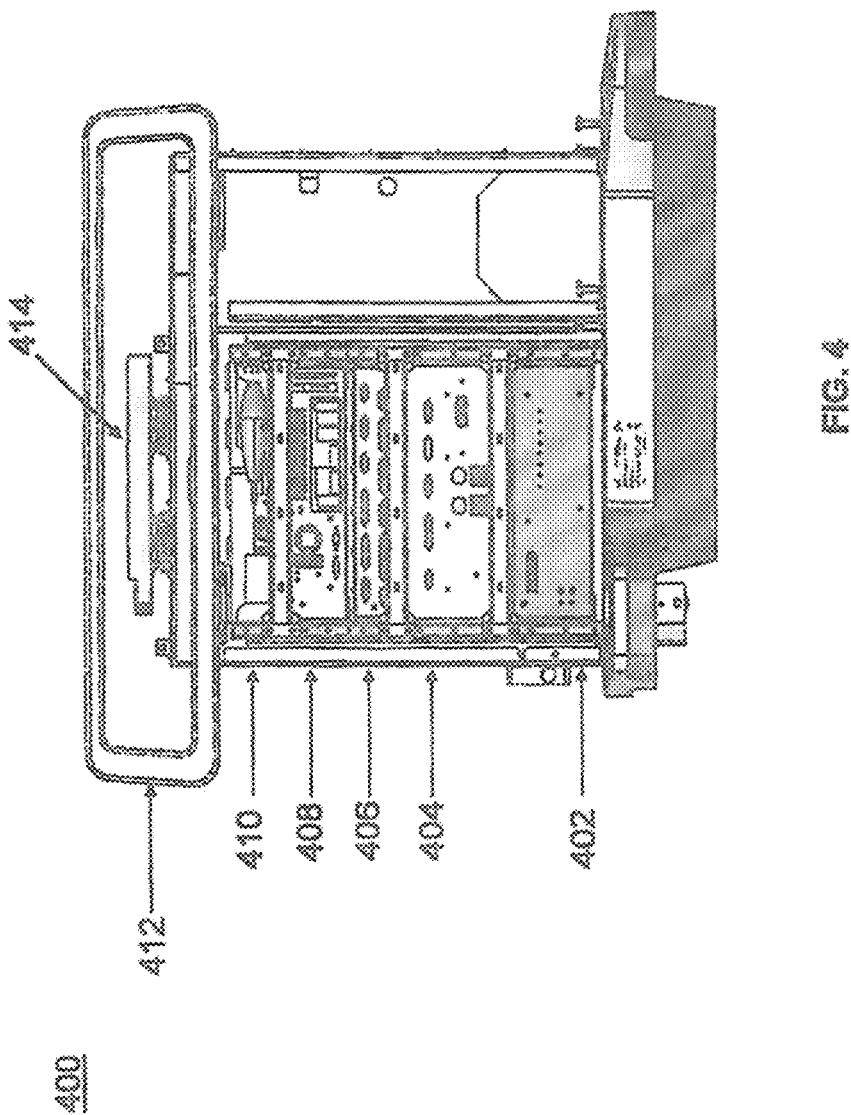
FIG. 4 illustrates a portion of a surgical robot in accordance with an exemplary embodiment.

Similar to surgical robot system 100, FIG. 3 illustrates a surgical robot system 300 and camera stand 302, in a docked configuration, consistent with an exemplary embodiment of the present disclosure. Surgical robot system 300 may comprise a robot 301 including a display 304, upper arm 306, lower arm 308, end effector 310, vertical column 312, casters 314, cabinet 316, tablet drawer 318, connector panel 320, control panel 322, and ring of information 324. Camera stand 302 may comprise camera 326. These components are described in greater with respect to FIG. 5. FIG. 3 illustrates the surgical robot system 300 in a docked configuration where the camera stand 302 is nested with the robot 301, for example, when not in use. It will be appreciated by those skilled in the art that the camera 326 and robot 301 may be separated from one another and positioned at any appropriate location during the surgical procedure, for example, as shown in FIGS. 1 and 2. FIG. 4 illustrates a base 400 consistent with an exemplary embodiment of the present disclosure. Base 400 may be a portion of surgical robot system 300 and comprise cabinet 316. Cabinet 316 may house certain components of surgical robot system 300 including but not limited to a battery 402, a power distribution module 404, a platform interface board module 406, a computer 408, a handle 412, and a tablet drawer 414. The connections and relationship between these components is described in greater detail with respect to FIG. 5.

Figure 5:
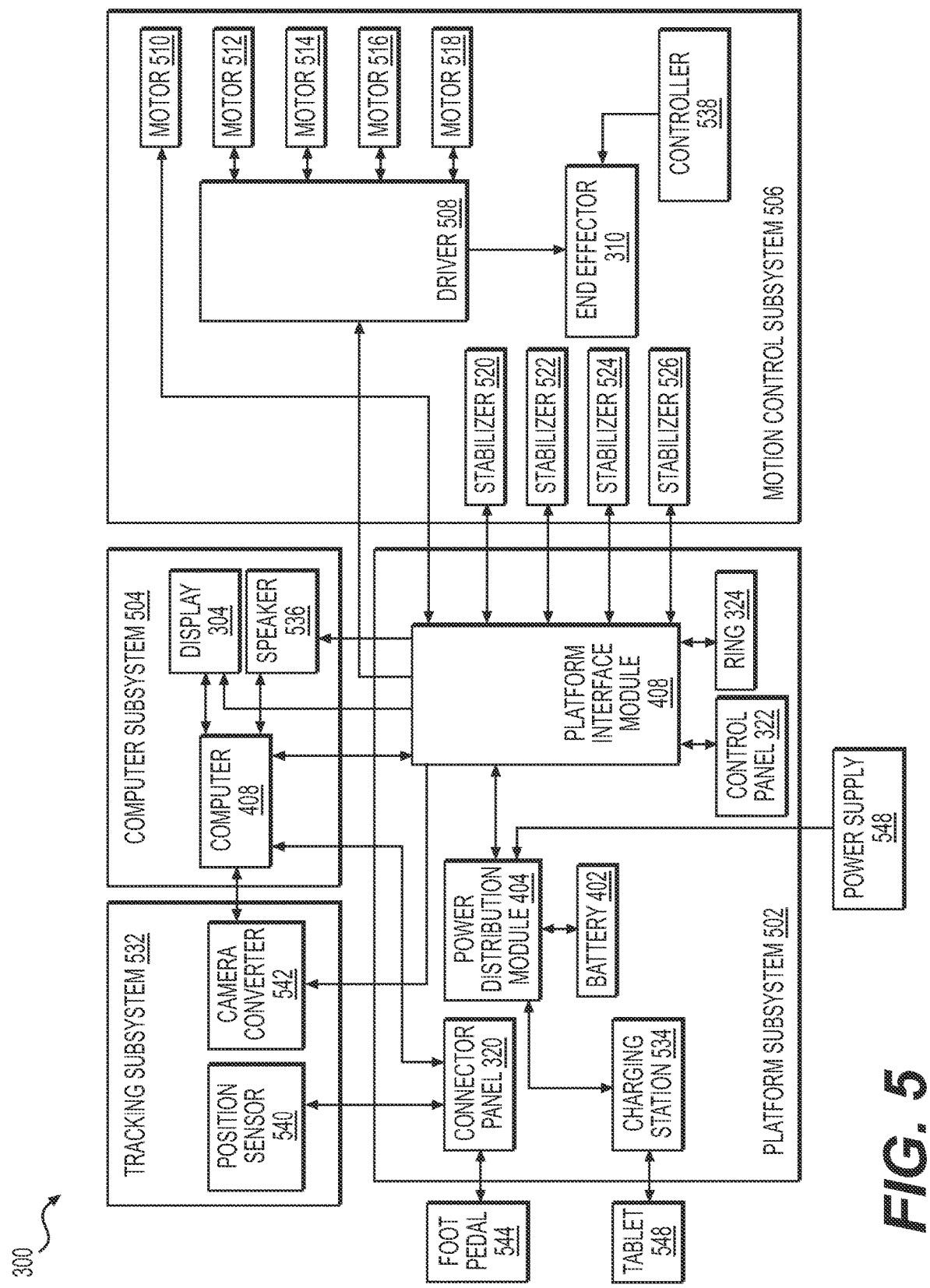
FIG. 5 illustrates a block diagram of a surgical robot in accordance with an exemplary embodiment.

FIG. 5 illustrates a block diagram of certain components of an exemplary embodiment of surgical robot system 300. Surgical robot system 300 may comprise platform subsystem 502, computer subsystem 504, motion control subsystem 506, and tracking subsystem 532. Platform subsystem 502 may further comprise battery 402, power distribution module 404, platform interface board module 406, and tablet charging station 534. Computer subsystem 504 may further comprise computer 408, display 304, and speaker 536. Motion control subsystem 506 may further comprise driver circuit 508, motors 510, 512, 514, 516, 518, stabilizers 520, 522, 524, 526, end effector 310, and controller 538. Tracking subsystem 532 may further comprise position sensor 540 and camera converter 542. System 300 may also comprise a foot pedal 544 and tablet 546.

Input power is supplied to system 300 via a power source 548 which may be provided to power distribution module 404. Power distribution module 404 receives input power and is configured to generate different power supply voltages that are provided to other modules, components, and subsystems of system 300. Power distribution module 404 may be configured to provide different voltage supplies to platform interface module 406, which may be provided to other components such as computer 408, display 304, speaker 536, driver 508 to, for example, power motors 512, 514, 516, 518 and end effector 310, motor 510, ring 324, camera converter 542, and other components for system 300 for example, fans for cooling the electrical components within cabinet 316.

Power distribution module 404 may also provide power to other components such as tablet charging station 534 that may be located within tablet drawer 318. Tablet charging station 534 may be in wireless or wired communication with tablet 546 for charging table 546. Tablet 546 may be used by a surgeon consistent with the present disclosure and described herein. Power distribution module 404 may also be connected to battery 402, which serves as temporary power source in the event that power distribution module 404 does not receive power from input power 548. At other times, power distribution module 404 may serve to charge battery 402 if necessary.

Other components of platform subsystem 502 may also include connector panel 320, control panel 322, and ring 324. Connector panel 320 may serve to connect different devices and components to system 300 and/or associated components and modules. Connector panel 320 may contain one or more ports that receive lines or connections from different components. For example, connector panel 320 may have a ground terminal port that may ground system 300 to other equipment, a port to connect foot pedal 544 to system 300, a port to connect to tracking subsystem 532, which may comprise position sensor 540, camera converter 542, and cameras 326 associated with camera stand 302. Connector panel 320 may also include other ports to allow USB, Ethernet, HDMI communications to other components, such as computer 408.

Control panel 322 may provide various buttons or indicators that control operation of system 300 and/or provide information regarding system 300. For example, control panel 322 may include buttons to power on or off system 300, lift or lower vertical column 312, and lift or lower stabilizers 520-526 that may be designed to engage casters 314 to lock system 300 from physically moving. Other buttons may stop system 300 in the event of an emergency, which may remove all motor power and apply mechanical brakes to stop all motion from occurring. Control panel 322 may also have indicators notifying the user of certain system conditions such as a line power indicator or status of charge for battery 402.

Ring 324 may be a visual indicator to notify the user of system 300 of different modes that system 300 is operating under and certain warnings to the user.

Computer subsystem 504 includes computer 408, display 304, and speaker 536. Computer 504 includes an operating system and software to operate system 300. Computer 504 may receive and process information from other components (for example, tracking subsystem 532, platform subsystem 502, and/or motion control subsystem 506) in order to display information to the user. Further, computer subsystem 504 may also include speaker 536 to provide audio to the user.

Tracking subsystem 532 may include position sensor 504 and converter 542. Tracking subsystem 532 may correspond to camera stand 302 including camera 326 as described with respect to FIG. 3. Position sensor 504 may be camera 326.

Tracking subsystem may track the location of certain markers that are located on the different components of system 300 and/or instruments used by a user during a surgical procedure. This tracking may be conducted in a manner consistent with the present disclosure including the use of infrared technology that tracks the location of active or passive elements, such as LEDs or reflective markers, respectively. The location, orientation, and position of structures having these types of markers may be provided to computer 408 which may be shown to a user on display 304. For example, a surgical instrument 608 having these types of markers and tracked in this manner (which may be referred to as a navigational space) may be shown to a user in relation to a three dimensional image of a patient's anatomical structure. Motion control subsystem 506 may be configured to physically move vertical column 312, upper arm 306, lower arm 308, or rotate end effector 310. The physical movement may be conducted through the use of one or more motors 510-518. For example, motor 510 may be configured to vertically lift or lower vertical column 312. Motor 512 may be configured to laterally move upper arm 308 around a point of engagement with vertical column 312 as shown in FIG. 3. Motor 514 may be configured to laterally move lower arm 308 around a point of engagement with upper arm 308 as shown in FIG. 3. Motors 516 and 518 may be configured to move end effector 310 in a manner such that one may control the roll and one may control the tilt, thereby providing multiple angles that end effector 310 may be moved. These movements may be achieved by controller 538 which may control these movements through load cells disposed on end effector 310 and activated by a user engaging these load cells to move system 300 in a desired manner.

Moreover, system 300 may provide for automatic movement of vertical column 312, upper arm 306, and lower arm 308 through a user indicating on display 304 (which may be a touchscreen input device) the location of a surgical instrument or component on three dimensional image of the patient's anatomy on display 304. The user may initiate this automatic movement by stepping on foot pedal 544 or some other input means.

Figure 6:
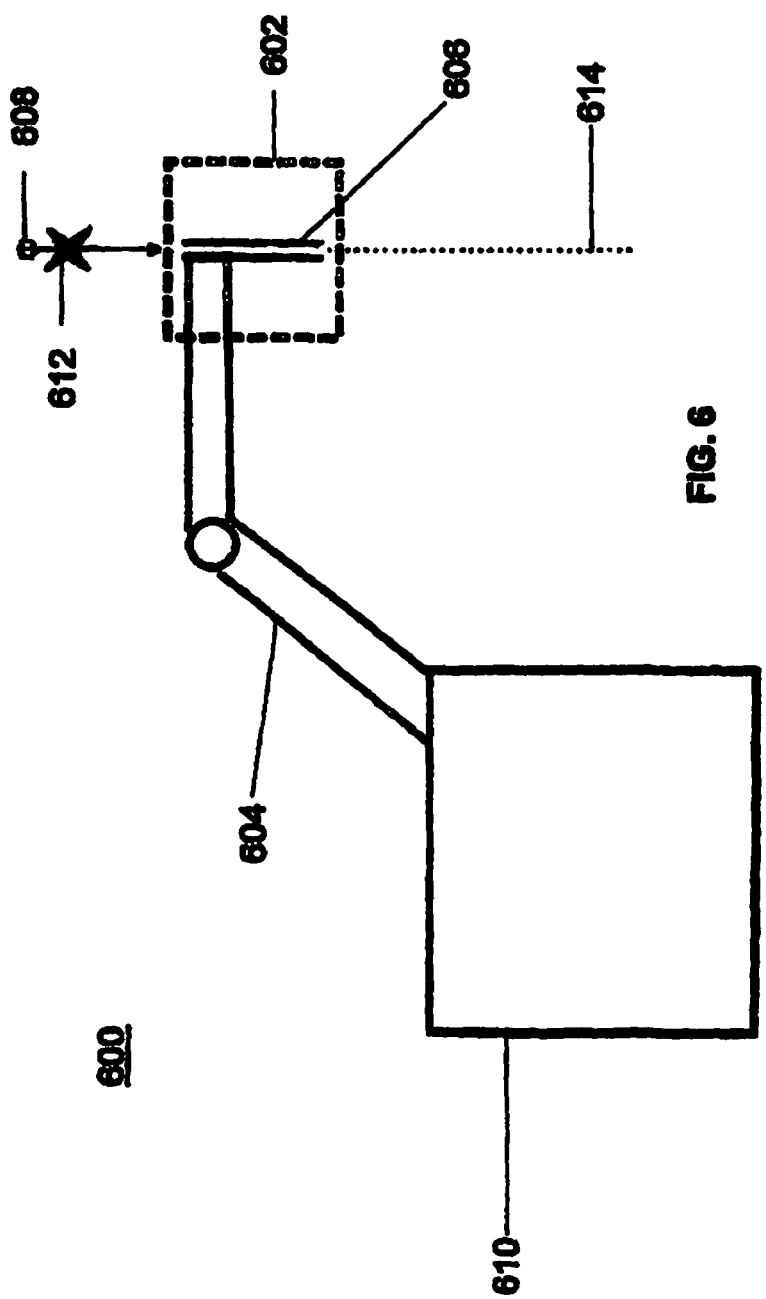
FIG. 6 illustrates a surgical robot in accordance with an exemplary embodiment.

FIG. 6 illustrates a surgical robot system 600 consistent with an exemplary embodiment. Surgical robot system 600 may comprise end effector 602, robot arm 604, guide tube 606, instrument 608, and robot base 610. Instrument tool 608 may be attached to a tracking array 612 including one or more tracking markers (such as markers 118) and have an associated trajectory 614. Trajectory 614 may represent a path of movement that instrument tool 608 is configured to travel once it is positioned through or secured in guide tube 606, for example, a path of insertion of instrument tool 608 into a patient. In an exemplary operation, robot base 610 may be configured to be in electronic communication with robot arm 604 and end effector 602 so that surgical robot system 600 may assist a user (for example, a surgeon) in operating on the patient 210. Surgical robot system 600 may be consistent with previously described surgical robot system 100 and 300.

Figure 8:
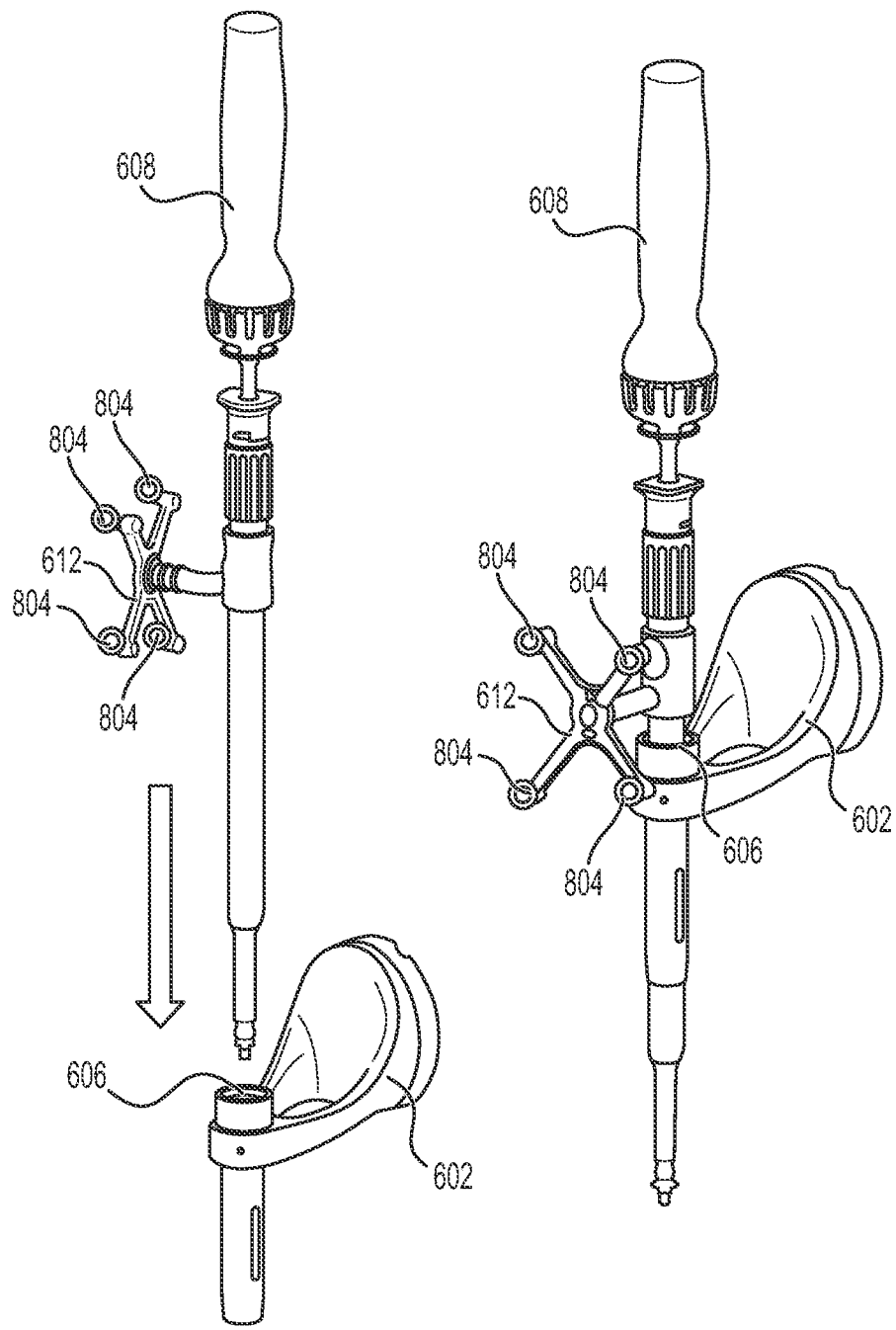
FIG. 8 illustrates a surgical instrument and the end effector, before and after, inserting the surgical instrument into the guide tube of the end effector according to one embodiment.

A tracking array 612 may be mounted on instrument 608 to monitor the location and orientation of instrument tool 608. The tracking array 612 may be attached to an instrument 608 and may comprise tracking markers 804. As best seen in FIG. 8, tracking markers 804 may be, for example, light emitting diodes and/or other types of reflective markers (e.g., markers 118 as described elsewhere herein). The tracking devices may be one or more line of sight devices associated with the surgical robot system. As an example, the tracking devices may be one or more cameras 200, 326 associated with the surgical robot system 100, 300 and may also track tracking array 612 for a defined domain or relative orientations of the instrument 608 in relation to the robot arm 604, the robot base 610, end effector 602, and/or the patient 210. The tracking devices may be consistent with those structures described in connection with camera stand 302 and tracking subsystem 532.

Figure 7:
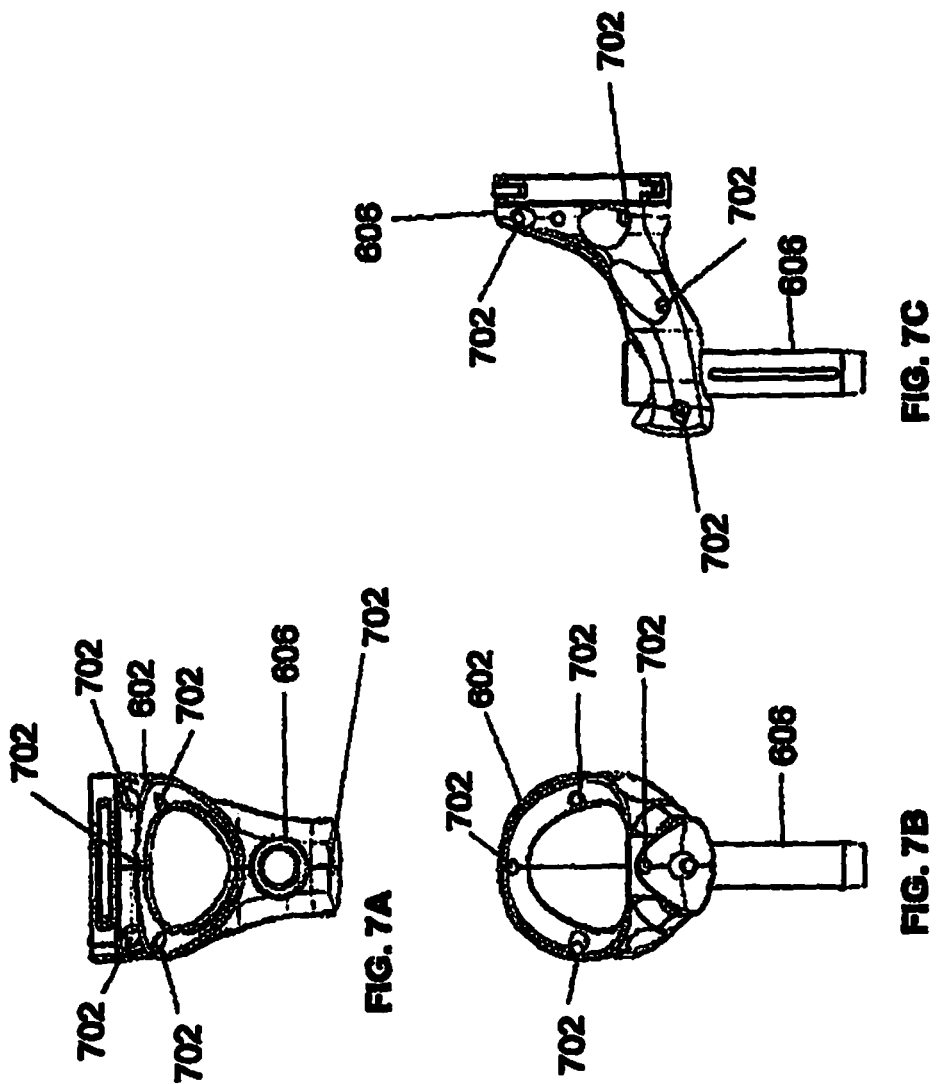
FIGS. 7A-7C illustrate an end effector in accordance with an exemplary embodiment.

FIGS. 7A, 7B, and 7C illustrate a top view, front view, and side view, respectively, of end effector 602 consistent with an exemplary embodiment. End effector 602 may comprise one or more tracking markers 702. Tracking markers 702 may be light emitting diodes or other types of active and passive markers, such as tracking markers 118 that have been previously described. In an exemplary embodiment, the tracking markers 702 are active infrared-emitting markers that are activated by an electrical signal (e.g., infrared light emitting diodes (LEDs)). Thus, tracking markers 702 may be activated such that the infrared markers 702 are visible to the camera 200, 326 or may be deactivated such that the infrared markers 702 are not visible to the camera 200, 326. Thus, when the markers 702 are active, the end effector 602 may be controlled by the system 100, 300, 600, and when the markers 702 are deactivated, the end effector 602 may be locked in position and unable to be moved by the system 100, 300, 600.

Markers 702 may be disposed on or within end effector 602 in a manner such that the markers 702 are visible by one or more cameras 200, 326 or other tracking devices associated with the surgical robot system 100, 300, 600. The camera 200, 326 or other tracking devices may track end effector 602 as it moves to different positions and viewing angles by following the movement of tracking markers 702. The location of markers 702 and/or end effector 602 may be shown on a display 110, 304 associated with the surgical robot system 100, 300, 600, for example, display 110 as shown in FIG. 2 and/or display 304 shown in FIG. 3. This display 110, 304 may allow a user to ensure that end effector 602 is in a desirable position in relation to robot arm 604, robot base 610, the patient 210, and/or the user.

For example, as shown in FIG. 7A, markers 702 may be placed around the surface of end effector 602 so that a tracking device placed away from the surgical field 208 and facing toward the robot 102, 301 and the camera 200, 326 is able to view at least 3 of the markers 702 through a range of common orientations of the end effector 602 relative to the tracking device 100, 300, 600. For example, distribution of markers 702 in this way allows end effector 602 to be monitored by the tracking devices when end effector 602 is translated and rotated in the surgical field 208.

In addition, in exemplary embodiments, end effector 602 may be equipped with infrared (IR) receivers that can detect when an external camera 200, 326 is getting ready to read markers 702. Upon this detection, end effector 602 may then illuminate markers 702. The detection by the IR receivers that the external camera 200, 326 is ready to read markers 702 may signal the need to synchronize a duty cycle of markers 702, which may be light emitting diodes, to an external camera 200, 326. This may also allow for lower power consumption by the robotic system as a whole, whereby markers 702 would only be illuminated at the appropriate time instead of being illuminated continuously. Further, in exemplary embodiments, markers 702 may be powered off to prevent interference with other navigation tools, such as different types of surgical instruments 608.

FIG. 8 depicts one type of surgical instrument 608 including a tracking array 612 and tracking markers 804. Tracking markers 804 may be of any type described herein including but not limited to light emitting diodes or reflective spheres. Markers 804 are monitored by tracking devices associated with the surgical robot system 100, 300, 600 and may be one or more of the line of sight cameras 200, 326. The cameras 200, 326 may track the location of instrument 608 based on the position and orientation of tracking array 612 and markers 804. A user, such as a surgeon 120, may orient instrument 608 in a manner so that tracking array 612 and markers 804 are sufficiently recognized by the tracking device or camera 200, 326 to display instrument 608 and markers 804 on, for example, display 110 of the exemplary surgical robot system.

The manner in which a surgeon 120 may place instrument 608 into guide tube 606 of the end effector 602 and adjust the instrument 608 is evident in FIG. 8. The hollow tube or guide tube 114, 606 of the end effector 112, 310, 602 is sized and configured to receive at least a portion of the surgical instrument 608. The guide tube 114, 606 is configured to be oriented by the robot arm 104 such that insertion and trajectory for the surgical instrument 608 is able to reach a desired anatomical target within or upon the body of the patient 210. The surgical instrument 608 may include at least a portion of a generally cylindrical instrument. Although a screw driver is exemplified as the surgical tool 608, it will be appreciated that any suitable surgical tool 608 may be positioned by the end effector 602. By way of example, the surgical instrument 608 may include one or more of a guide wire, cannula, a retractor, a drill, a reamer, a screw driver, an insertion tool, a removal tool, or the like. Although the hollow tube 114, 606 is generally shown as having a cylindrical configuration, it will be appreciated by those of skill in the art that the guide tube 114, 606 may have any suitable shape, size and configuration desired to accommodate the surgical instrument 608 and access the surgical site.

Figure 9:
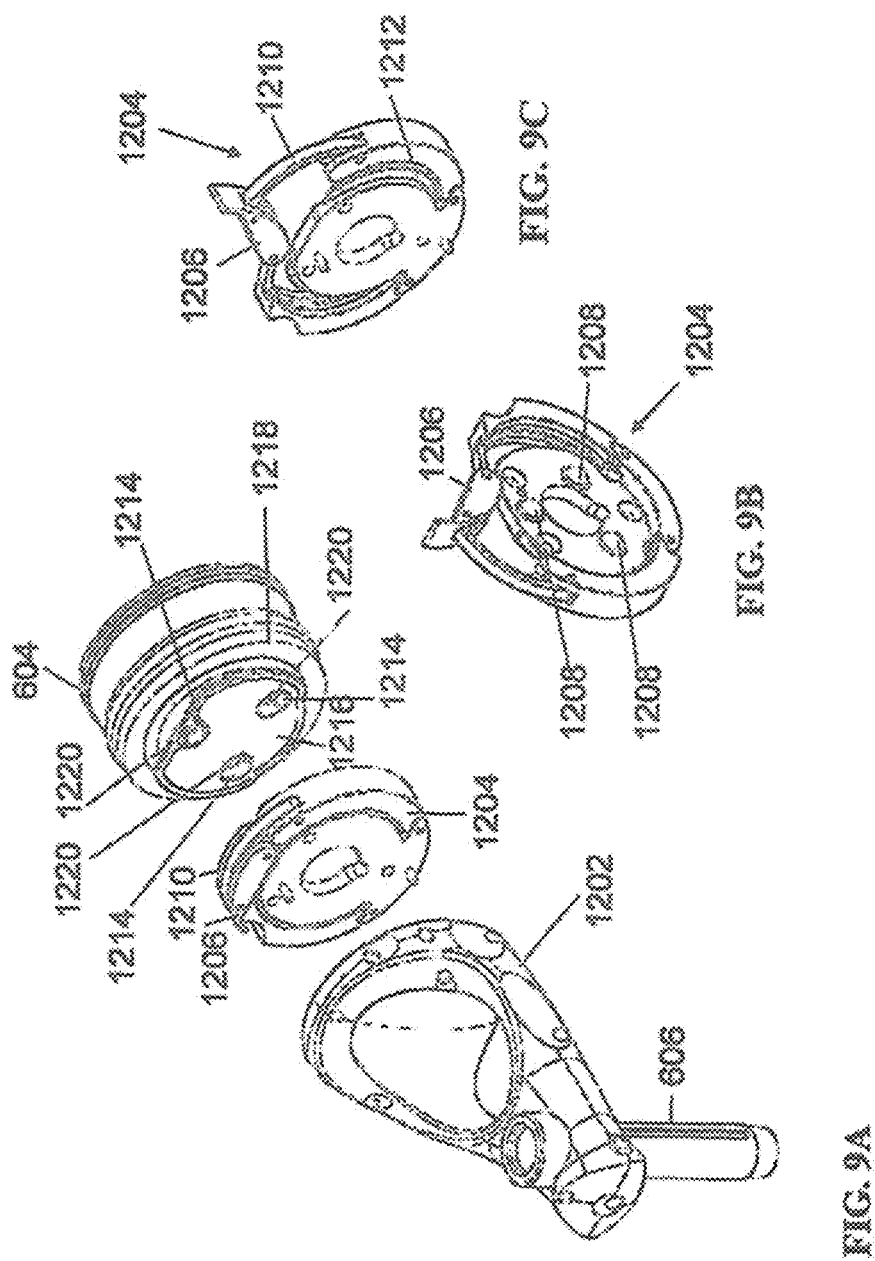
FIGS. 9A-9C illustrate portions of an end effector and robot arm in accordance with an exemplary embodiment.

FIGS. 9A-9C illustrate end effector 602 and a portion of robot arm 604 consistent with an exemplary embodiment. End effector 602 may further comprise body 1202 and clamp 1204. Clamp 1204 may comprise handle 1206, balls 1208, spring 1210, and lip 1212. Robot arm 604 may further comprise depressions 1214, mounting plate 1216, lip 1218, and magnets 1220.

End effector 602 may mechanically interface and/or engage with the surgical robot system and robot arm 604 through one or more couplings. For example, end effector 602 may engage with robot arm 604 through a locating coupling and/or a reinforcing coupling. Through these couplings, end effector 602 may fasten with robot arm 604 outside a flexible and sterile barrier. In an exemplary embodiment, the locating coupling may be a magnetically kinematic mount and the reinforcing coupling may be a five bar over center clamping linkage.

With respect to the locating coupling, robot arm 604 may comprise mounting plate 1216, which may be non-magnetic material, one or more depressions 1214, lip 1218, and magnets 1220. Magnet 1220 is mounted below each of depressions 1214. Portions of clamp 1204 may comprise magnetic material and be attracted by one or more magnets 1220. Through the magnetic attraction of clamp 1204 and robot arm 604, balls 1208 become seated into respective depressions 1214. For example, balls 1208 as shown in FIG. 9B would be seated in depressions 1214 as shown in FIG. 9A. This seating may be considered a magnetically-assisted kinematic coupling. Magnets 1220 may be configured to be strong enough to support the entire weight of end effector 602 regardless of the orientation of end effector 602. The locating coupling may be any style of kinematic mount that uniquely restrains six degrees of freedom.

With respect to the reinforcing coupling, portions of clamp 1204 may be configured to be a fixed ground link and as such clamp 1204 may serve as a five bar linkage. Closing clamp handle 1206 may fasten end effector 602 to robot arm 604 as lip 1212 and lip 1218 engage clamp 1204 in a manner to secure end effector 602 and robot arm 604. When clamp handle 1206 is closed, spring 1210 may be stretched or stressed while clamp 1204 is in a locked position. The locked position may be a position that provides for linkage past center. Because of a closed position that is past center, the linkage will not open absent a force applied to clamp handle 1206 to release clamp 1204. Thus, in a locked position end effector 602 may be robustly secured to robot arm 604.

Spring 1210 may be a curved beam in tension. Spring 1210 may be comprised of a material that exhibits high stiffness and high yield strain such as virgin PEEK (poly-ether-ether-ketone). The linkage between end effector 602 and robot arm 604 may provide for a sterile barrier between end effector 602 and robot arm 604 without impeding fastening of the two couplings.

The reinforcing coupling may be a linkage with multiple spring members. The reinforcing coupling may latch with a cam or friction based mechanism. The reinforcing coupling may also be a sufficiently powerful electromagnet that will support fastening end-effector 102 to robot arm 604. The reinforcing coupling may be a multi-piece collar completely separate from either end effector 602 and/or robot arm 604 that slips over an interface between end effector 602 and robot arm 604 and tightens with a screw mechanism, an over center linkage, or a cam mechanism.

Figure 10:
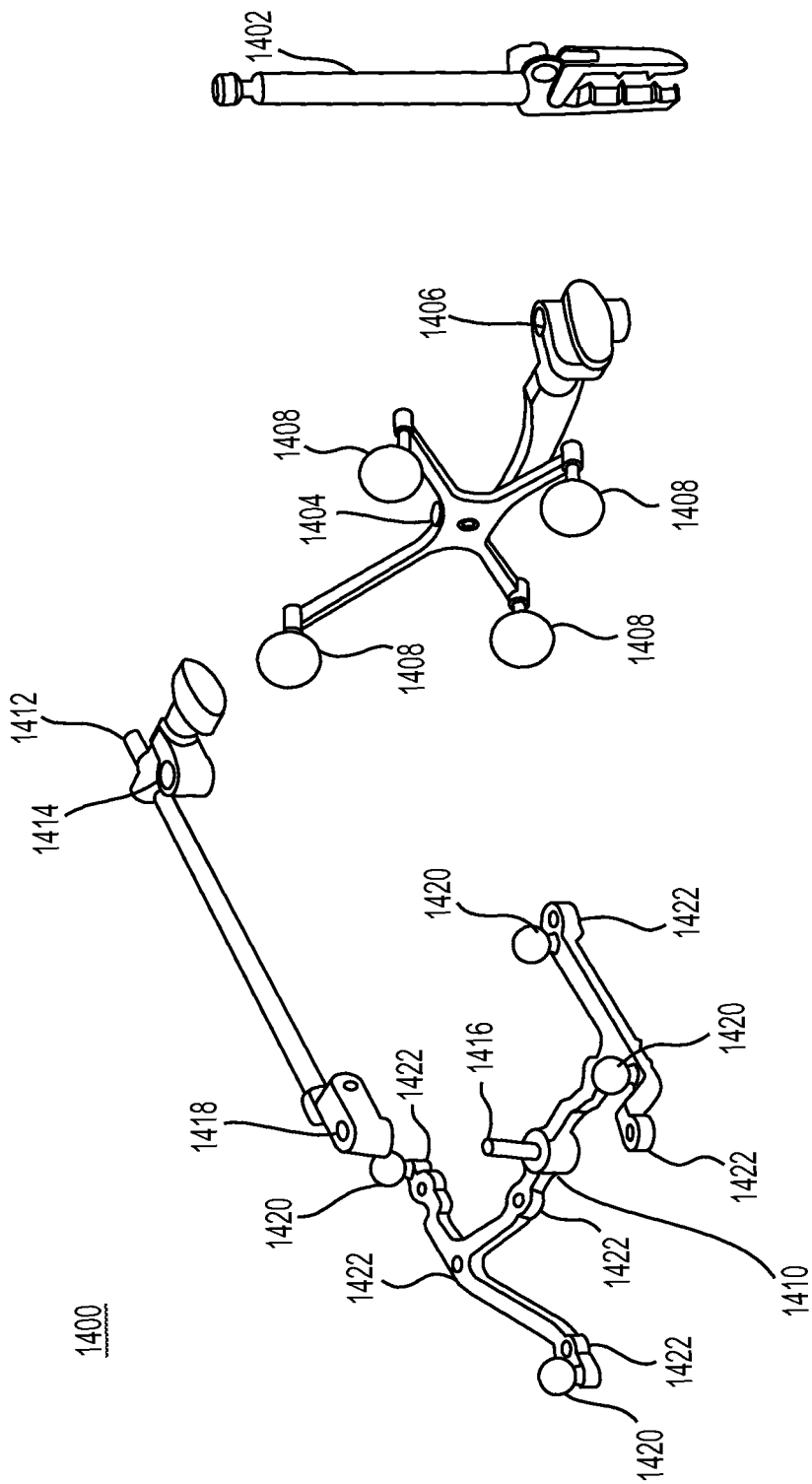
FIG. 10 illustrates a dynamic reference array, an imaging array, and other components in accordance with an exemplary embodiment.
Figure 11:
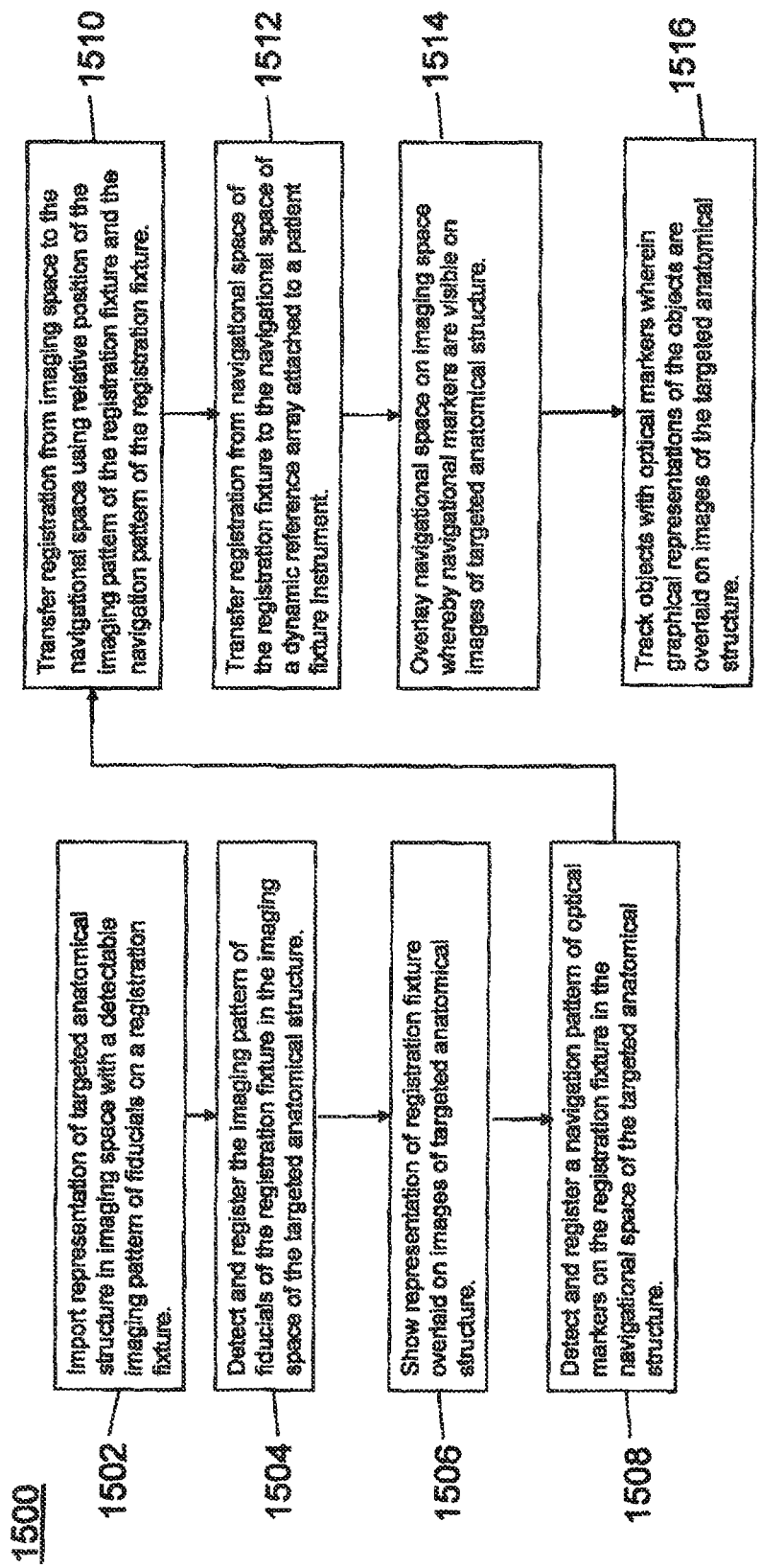
FIG. 11 illustrates a method of registration in accordance with an exemplary embodiment.

Referring to FIGS. 10 and 11, prior to or during a surgical procedure, certain registration procedures may be conducted in order to track objects and a target anatomical structure of the patient 210 both in a navigation space and an image space. In order to conduct such registration, a registration system 1400 may be used as illustrated in FIG. 10.

In order to track the position of the patient 210, a patient tracking device 116 may include a patient fixation instrument 1402 to be secured to a rigid anatomical structure of the patient 210 and a dynamic reference base (DRB) 1404 may be securely attached to the patient fixation instrument 1402. For example, patient fixation instrument 1402 may be inserted into opening 1406 of dynamic reference base 1404. Dynamic reference base 1404 may contain markers 1408 that are visible to tracking devices, such as tracking subsystem 532. These markers 1408 may be optical markers or reflective spheres, such as tracking markers 118, as previously discussed herein.

Patient fixation instrument 1402 is attached to a rigid anatomy of the patient 210 and may remain attached throughout the surgical procedure. In an exemplary embodiment, patient fixation instrument 1402 is attached to a rigid area of the patient 210, for example, a bone that is located away from the targeted anatomical structure subject to the surgical procedure. In order to track the targeted anatomical structure, dynamic reference base 1404 is associated with the targeted anatomical structure through the use of a registration fixture that is temporarily placed on or near the targeted anatomical structure in order to register the dynamic reference base 1404 with the location of the targeted anatomical structure.

A registration fixture 1410 is attached to patient fixation instrument 1402 through the use of a pivot arm 1412. Pivot arm 1412 is attached to patient fixation instrument 1402 by inserting patient fixation instrument 1402 through an opening 1414 of registration fixture 1410. Pivot arm 1412 is attached to registration fixture 1410 by, for example, inserting a knob 1416 through an opening 1418 of pivot arm 1412.

Using pivot arm 1412, registration fixture 1410 may be placed over the targeted anatomical structure and its location may be determined in an image space and navigation space using tracking markers 1420 and/or fiducials 1422 on registration fixture 1410. Registration fixture 1410 may contain a collection of markers 1420 that are visible in a navigational space (for example, markers 1420 may be detectable by tracking subsystem 532). Tracking markers 1420 may be optical markers visible in infrared light as previously described herein. Registration fixture 1410 may also contain a collection of fiducials 1422, for example, such as bearing balls, that are visible in an imaging space (for example, a three dimension CT image). As described in greater detail with respect to FIG. 11, using registration fixture 1410, the targeted anatomical structure may be associated with dynamic reference base 1404 thereby allowing depictions of objects in the navigational space to be overlaid on images of the anatomical structure. Dynamic reference base 1404, located at a position away from the targeted anatomical structure, may become a reference point thereby allowing removal of registration fixture 1410 and/or pivot arm 1412 from the surgical area.

FIG. 11 provides an exemplary method 1500 for registration consistent with the present disclosure. Method 1500 begins at step 1502 wherein a graphical representation (or image(s)) of the targeted anatomical structure may be imported into system 100, 300 600, for example computer 408. The graphical representation may be three dimensional CT or a fluoroscope scan of the targeted anatomical structure of the patient 210 which includes registration fixture 1410 and a detectable imaging pattern of fiducials 1420.

At step 1504, an imaging pattern of fiducials 1420 is detected and registered in the imaging space and stored in computer 408. Optionally, at this time at step 1506, a graphical representation of the registration fixture 1410 may be overlaid on the images of the targeted anatomical structure.

At step 1508, a navigational pattern of registration fixture 1410 is detected and registered by recognizing markers 1420. Markers 1420 may be optical markers that are recognized in the navigation space through infrared light by tracking subsystem 532 via position sensor 540. Thus, the location, orientation, and other information of the targeted anatomical structure is registered in the navigation space. Therefore, registration fixture 1410 may be recognized in both the image space through the use of fiducials 1422 and the navigation space through the use of markers 1420. At step 1510, the registration of registration fixture 1410 in the image space is transferred to the navigation space. This transferal is done, for example, by using the relative position of the imaging pattern of fiducials 1422 compared to the position of the navigation pattern of markers 1420.

At step 1512, registration of the navigation space of registration fixture 1410 (having been registered with the image space) is further transferred to the navigation space of dynamic registration array 1404 attached to patient fixture instrument 1402. Thus, registration fixture 1410 may be removed and dynamic reference base 1404 may be used to track the targeted anatomical structure in both the navigation and image space because the navigation space is associated with the image space.

At steps 1514 and 1516, the navigation space may be overlaid on the image space and objects with markers visible in the navigation space (for example, surgical instruments 608 with optical markers 804). The objects may be tracked through graphical representations of the surgical instrument 608 on the images of the targeted anatomical structure.

Figure 12A:
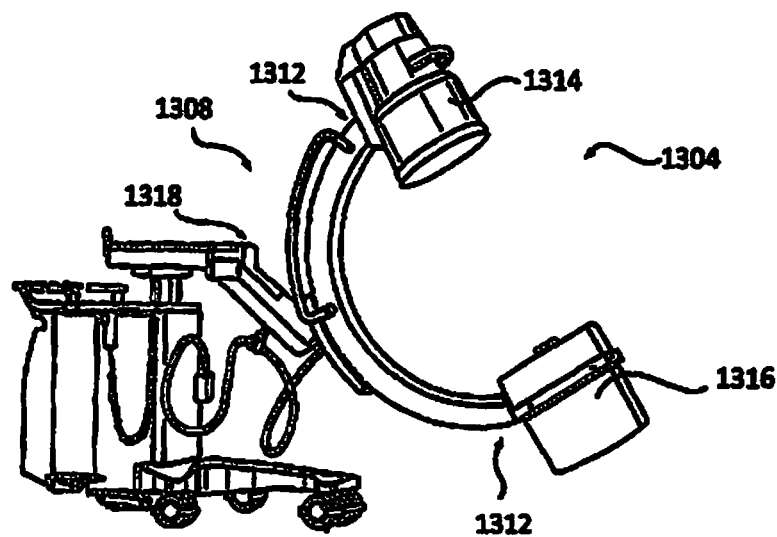
FIGS. 12A-12B illustrate embodiments of imaging devices according to exemplary embodiments.
Figure 12B:
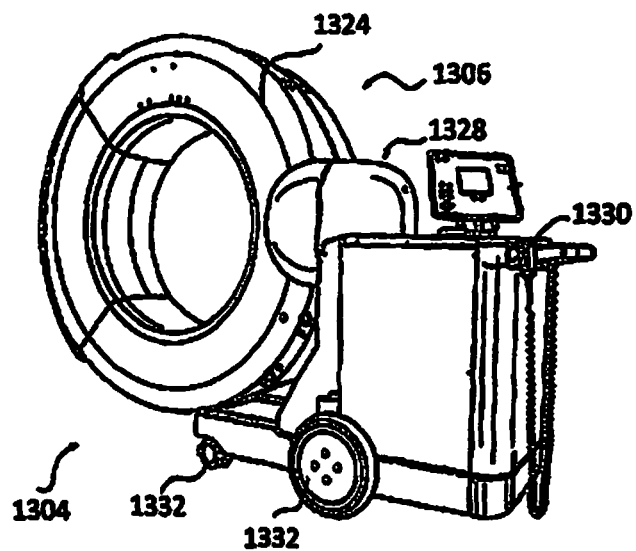

FIGS. 12A-12B illustrate imaging devices 1304 that may be used in conjunction with robot systems 100, 300, 600 to acquire pre-operative, intra-operative, post-operative, and/or real-time image data of patient 210. Any appropriate subject matter may be imaged for any appropriate procedure using the imaging system 1304. The imaging system 1304 may be any imaging device such as imaging device 1306 and/or a C-arm 1308 device. It may be desirable to take x-rays of patient 210 from a number of different positions, without the need for frequent manual repositioning of patient 210 which may be required in an x-ray system. As illustrated in FIG. 12A, the imaging system 1304 may be in the form of a C-arm 1308 that includes an elongated C-shaped member terminating in opposing distal ends 1312 of the "C" shape. C-shaped member 1130 may further comprise an x-ray source 1314 and an image receptor 1316. The space within C-arm 1308 of the arm may provide room for the physician to attend to the patient substantially free of interference from x-ray support structure 1318. As illustrated in FIG. 12B, the imaging system may include imaging device 1306 having a gantry housing 1324 attached to a support structure imaging device support structure 1328, such as a wheeled mobile cart 1330 with wheels 1332, which may enclose an image capturing portion, not illustrated. The image capturing portion may include an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of patient 210 to be acquired from multiple directions or in multiple planes. Although certain imaging systems 1304 are exemplified herein, it will be appreciated that any suitable imaging system may be selected by one of ordinary skill in the art.

Referring now to FIGS. 13A-15 of the present disclosure, exemplary embodiments of a surveillance marker consistent with the present disclosure are illustrated. FIGS. 13A-13B depicts a system 2000 including a surveillance maker 2002, a dynamic reference base (DRB) 2004, which may be a tracking array having array markers 2006, a DRB post 2008, and a surveillance marker post 2010. Also depicted is a patient's bone 2012. In this configuration, surveillance marker 2002 is on surveillance marker post 2010 that is within the hollow center or channel of the main shaft of the DRB post 2008. Surveillance marker post 2010 could consist of hard metal with a sharp, smooth tip for driving into bone with a mallet, or an end-threaded tip for drilling into bone. If DRB 2004 is bumped or dislodged, the tracking array with array markers 2006 would shift relative to the position of surveillance marker 2002 despite the close proximity of the spikes holding DRB 2004 to bone 2012 and the tip of the surveillance post 2010 for the surveillance marker 2002. Post 2010 to which surveillance marker 2002 is mounted is within the hollow main shaft of a spike or clamp to which DRB 2004 is mounted. There may be a loose tolerance between the wall of the hollow main shaft of DRB post 2008 and surveillance marker post 2010.

In the exemplary embodiment of FIG. 13A, with surveillance marker post 2010 encompassed by DRB post 2008, dislodgment and bending movement of DRB 2004 may cause DRB 2004 to press against surveillance marker post 2010 and cause it to move as well. However, since the attachment or entry point to bone 2012 is different for DRB post 2008 and surveillance marker post 2010, the axis of rotation of surveillance marker post 2010 and DRB 2004 may differ, meaning there may be a detectable change in position of surveillance marker 2002 relative to DRB 2004 even if the two structures touch. The amount of relative shift in position of surveillance marker 2002 and tracking markers 2006 if DRB 2004 is bumped may be greatest if surveillance marker post 2010 does not touch the inside wall of the hollow shaft of DRB post 2008. It may be beneficial to have a loose tolerance between surveillance marker post 2010 and inside wall of the DRB post 2010 for a more easily detectable effect. It may also be beneficial to at least begin surveillance with a condition where surveillance marker post 2010 is not touching the hollow wall of DRB post 2004, even if it will eventually touch during bending. To help ensure that surveillance marker post 2010 is not touching the hollow wall of DRB post 2008 during insertion, it may be beneficial to use a temporary centering guide such as a doughnut-shaped piece, through which surveillance marker post 2008 is inserted and which forces the surveillance marker post to the midline of the hollow shaft. After the post is inserted, the guide could be removed so that there remains loose tolerance between the hollow wall of the DRB post 2008 and surveillance marker post 2010. Such a guide could be used at the top of the DRB's tube region, at the bottom of the tube region, or both.

FIG. 13B is another configuration of system 2000 with surveillance marker 2002 offset from the midline of DRB post 2008. This configuration may avoid inadvertent rotation of the clamped DRB 2004 about the axis of the shaft when bumped. Such rotation may occur if clamp 2014 holding DRB 2004 in place is not sufficiently tightened and DRB 2004 is disturbed, even slightly. In the exemplary embodiment of FIG. 13A, if rotation of DRB 2004 about DRB post 2008 occurred without any travel of DRB 2004 longitudinally along DRB post 2008, there may be minimal or undetectable relative movement of surveillance marker 2002 during rotational dislodgement since the position of surveillance marker 2002 is on or close to the axis of rotation of DRB 2004 rotational movement. In this event, surveillance marker 2002 may be offset from the midline or longitudinal axis of DRB post 2008 (for example by 1 cm or more), as shown in FIG. 13B. In this configuration, even a slight rotation of DRB 2004 about its mounting shaft would be detectable relative to the unmoved surveillance marker 2002, since surveillance marker 2002 is not on the axis of rotation of DRB 2004. This configuration may also give a distal region on surveillance marker post 2010 that can serve as the head to be struck with a hammer for driving it into bone, or a region to clamp in the chuck of a drill if it is to be drilled into bone. If surveillance marker 2002 is attached centrally to post 2010, a cap or other feature may be added to allow it to be inserted without damaging the surface of surveillance marker 2002, which may be coated with reflective paint. Additionally, during insertion, this configuration may allow surveillance marker 2002 to be manually rotated and positioned pointing toward the tracking cameras for better visibility.

FIGS. 14A-B illustrates an exemplary embodiment of a system 2100 that includes some components as previously described. System 2100 also includes a temporary grouping element 2102. In system 2100, surveillance marker 2002 may be attached through the same incision into a patient, but not physically connected to DRB 2004 or DRB post 2008. One manner to do this may be to use temporary grouping element 2102 to hold surveillance post 2010 and DRB post 2008 so that these components may be inserted as a unit. These components may then become independent after temporary grouping element 2102 is removed as shown in FIG. 14B.

In FIG. 14A, DRB post 2008 and surveillance marker post 2010 may be inserted into bone 2012 simultaneously while being held together at a desired spacing with temporary grouping element 2102. After DRB post 2008 and surveillance marker post 2010 have been inserted, temporary grouping element 2102 may be removed, and DRB 2004 and surveillance marker 2002 may be attached, which may be anchored in independent pieces of bone. Temporary grouping element 2102 may also be an impaction cap to be struck by a hammer during insertion.

Figure 15:
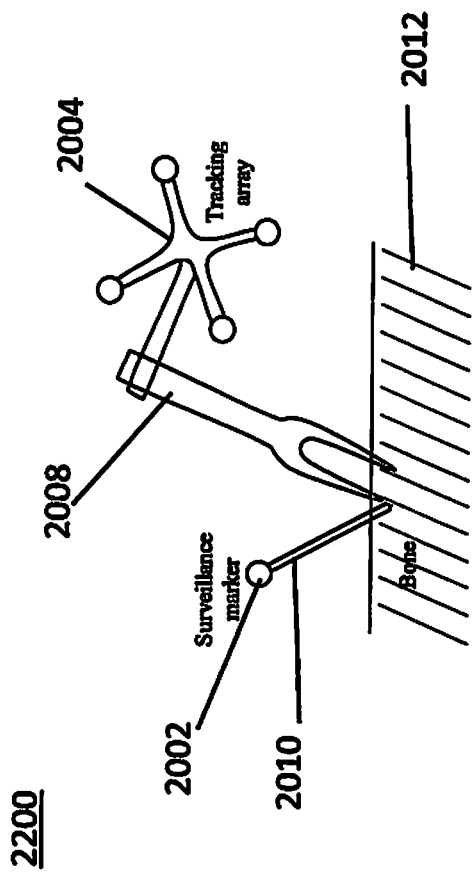
FIG. 15 illustrates a surveillance marker in accordance with an exemplary embodiment of the present disclosure.

FIG. 15 illustrates an exemplary embodiment 2200. In this configuration it may be possible to attach surveillance marker 2002 through the same incision of the patient but not physically connected to DRB 2004. In FIG. 15, different insertion angles may be used, with trajectories of the surveillance marker post 2010 and DRB post 2008 within the same incision (not shown).

The attachment of surveillance marker 2002 as described with regard to FIGS. 13-15 may allow application of a surveillance marker, which has demonstrated benefits, through a single incision instead of requiring multiple incisions which may result in less time in surgery and less discomfort for the patient.

Figure 16A:
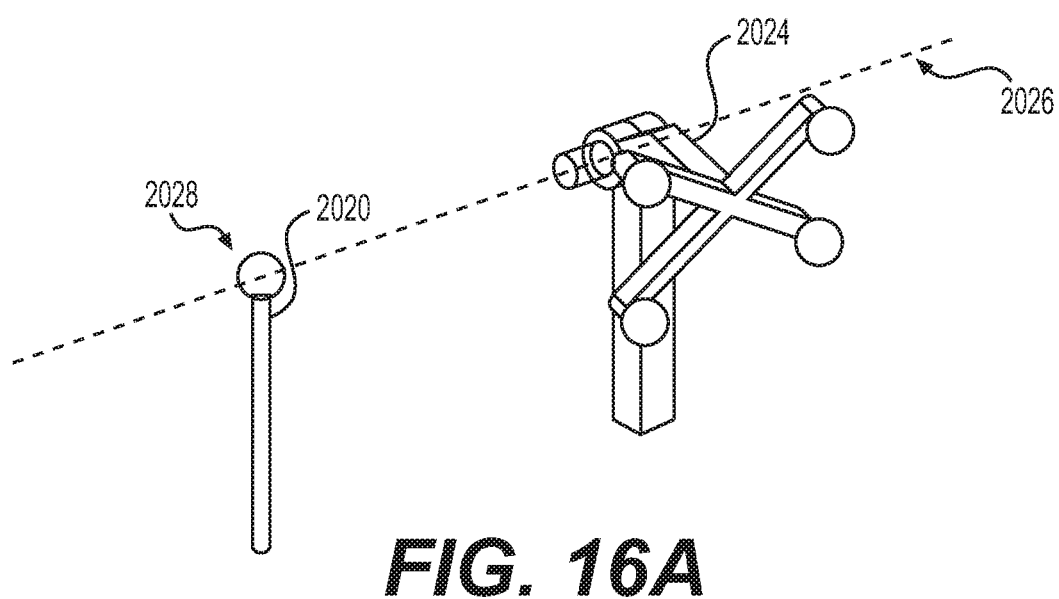
FIGS. 16A and 16B illustrates a surveillance marker in accordance in one embodiment of the present disclosure.
Figure 16B:
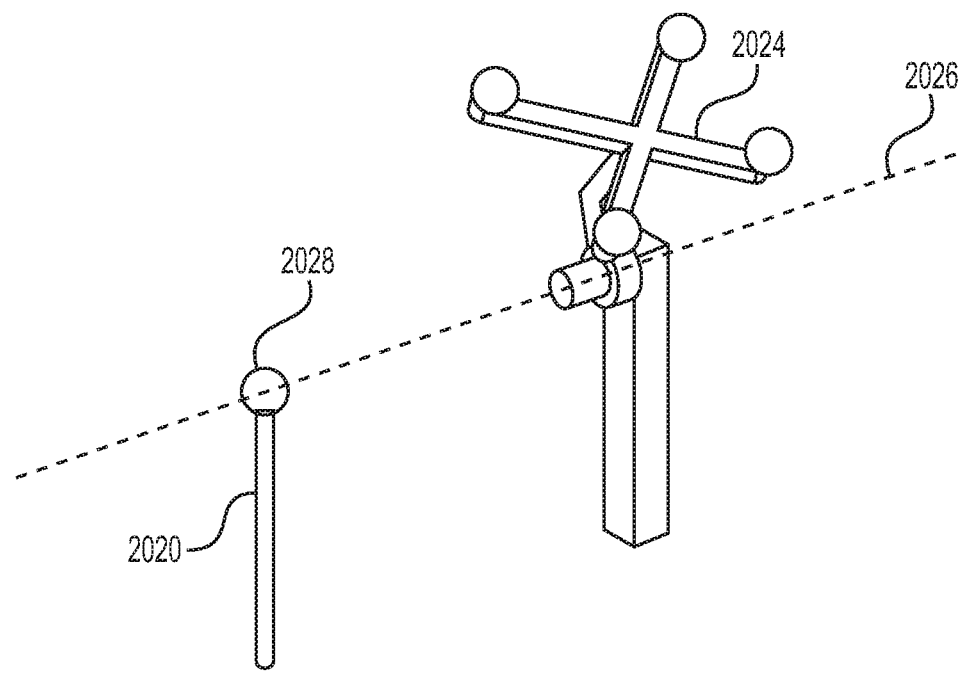

Now turning to FIGS. 16A and 16B, there is shown a surveillance marker 2020 that is used to detect any change of position of the dynamic reference base (DRB) 2024, which is critical for navigational accuracy. In some situations, the surveillance marker 2020 may not be able to detect a position change correctly if a DRB rotates along an axis 2026, and the surveillance marker 2020 is close to or on the axis of rotation 2026. The change of position appears as a rotation of the surveillance marker 2020, which does not register as a position change, since the surveillance marker 2020 is a configured as a sphere.

The surveillance marker 2020 as illustrated in FIGS. 16A and 16B, uses a single optical marker 2028, typically a sphere, 'registered' to the DRB 2024. Both surveillance marker and DRB are securely attached to bony anatomy with a separate post or spike. The position of the surveillance marker is tracked with respect to the DRB 2024 coordinate system, so that any shift or rotation of the DRB 2024 (or any shift of the surveillance marker) can be detected, even if the camera is moved. This scheme works well in any situation involving a purely translational shift.

Figures 17A, 17B:
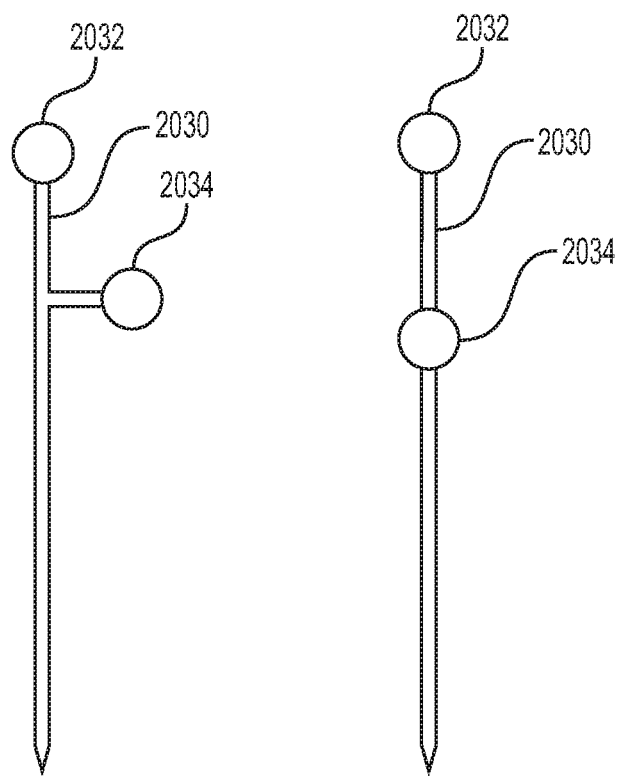
FIGS. 17A and 17B illustrates a surveillance marker in accordance with an exemplary embodiment of the present disclosure.

FIGS. 16A and 16B show how a single surveillance marker fails to detect the rotation of an array on a DRB if the DRB mounts to the patient with a hinge mechanism and the hinge's axis of rotation intersects the surveillance marker. However, if more than one surveillance marker is used, the system can successfully detect a rotation, if the axis of rotation of the DRB does not pass through all the surveillance markers. In one exemplary embodiment, this mechanism would utilize two optical markers on the surveillance instrument, which could attach to the same post as shown in FIGS. 17A and 17B to minimize surgical incisions or mounted to different posts. In this embodiment, a surveillance marker 2030 is provided with at least two optical markers 2032, 2034. The system could use the relative distance between each of optical markers 2032, 2034 and the DRB, or between the line formed by the two markers 2032, 2034 and the DRB markers, to calculate the amount of shift.

Surveillance markers mounted to a post vertically or mostly vertically as shown in FIG. 17 will most likely not both be collinear with a hinge that is oriented horizontally. In other embodiments, three or more markers may be used to create accuracy through redundancy.

Figure 18:
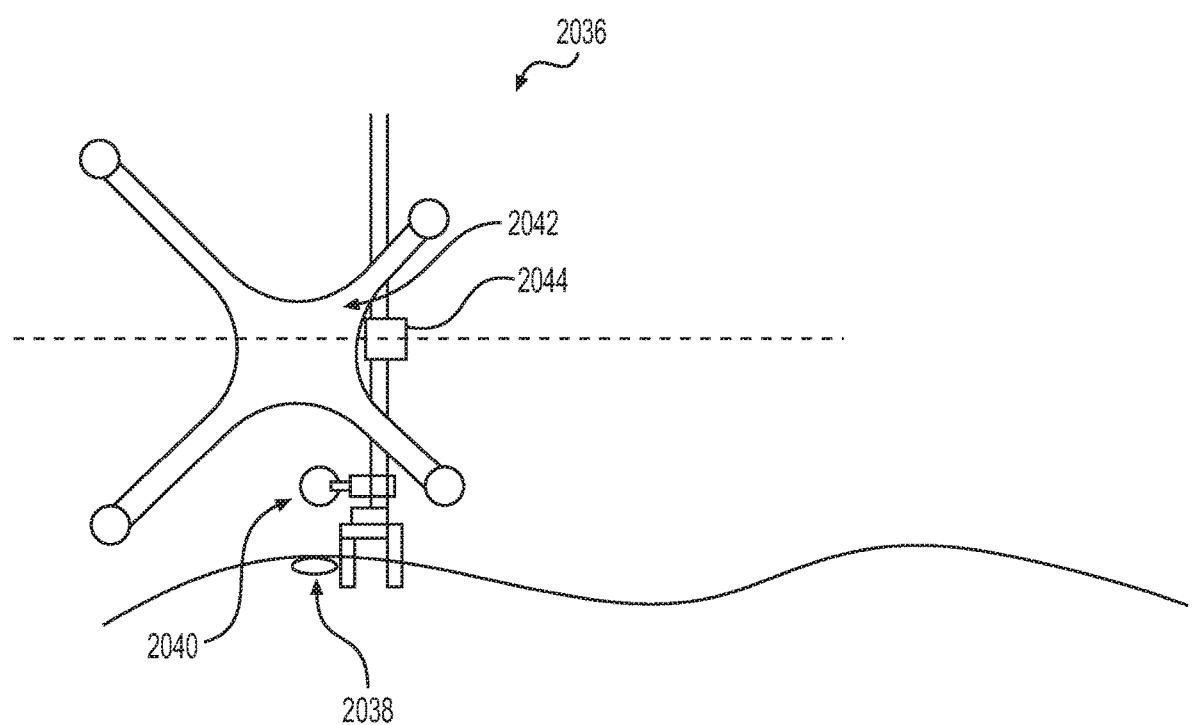
FIG. 18 illustrates yet another embodiment of a multiple surveillance markers in accordance with an embodiment of the present disclosure.

Now turning to FIG. 18, in a preferred embodiment, the system through a software element may alert the user that a single surveillance marker 2040 is in close proximity to the axis of rotation of the DRB 2042 if the location of the DRB's hinge 2044 is known relative to the tracked markers of the DRB 2042 and hinge location is extrapolated and compared to the surveillance marker position 2040. If the surveillance marker 2040 is close to the hinge, for example in one embodiment less than 25 mm from the hinge, the system can alert the user to move the surveillance marker or use a secondary method such as landmark check to test whether there is any rotational movement. Similarly, the system can alert the user if dual surveillance markers form a line that is close to being collinear with the hinge of the DRB.

In another embodiment, the system provides a method of ensuring that the DRB hinge does not intersect the surveillance marker by restricting where the user can mount the surveillance marker to force the surveillance marker to be located away from the DRB's hinge. In one particular embodiment, a collar clamp on the DRB shaft with a small post present for the attachment of a single surveillance marker is used (FIG. 3). There are markings provided on the DRB shaft and physical stops along the shaft or collar, or in another embodiment a wide collar clamp design ensure that the surveillance marker is never able to be mounted far enough up the shaft that it would approach the location of the hinge.

In another embodiment, there is a provided a method of preventing the surveillance marker from approaching the hinge. A temporary guide tube is utilized wherein the temporary guide tube has a minimum allowable radius to the hinge during setup, blocking the user from placing the surveillance marker within that radius of the hinge.

In yet another embodiment, a chain or other tether to the base of the DRB with the surveillance marker attached to the other end could be used that will not allow the surveillance marker to approach the hinge location.

When the DRB is displaced either accidentally or by need, the present system provides a method of monitoring skin movement. In one embodiment, the skin may be marked with ink 2040 or any other bio-compatible material or a second surveillance marker may be attached to the skin (FIG. 3). If a first surveillance marker is already near the skin, like in the previous, embodiment, the mark on the skin can be placed very near the post-mounted marker. The system would be able to use the first surveillance marker mounted to the DRB post to track DRB shift and rotation, while the surgeon would visually monitor the patient's skin mark to track shift (tugging) of the skin immediately surrounding the DRB. The close proximity of the skin mark or the second surveillance market to the first surveillance marker makes it is easier to visualize for the surgeon to discern a shift. If the surgeon suspected that the ink mark or the second surveillance marker has shifted, the surgeon or user can point to the skin mark or the second surveillance marker with a tracked probe to determine how much it had moved relative to the location of the probe at the beginning of the case. If a tracked marker on the skin is used, this marker can continuously monitor the relationship between the DRB post and the skin to assess whether there is offset. The above embodiments provide the advantage of tracking the shift in the surveillance marker relative to the DRB even in the cases where the shift is in the surveillance marker. In addition, multiple surveillance markers provide redundancy to the system when line of sight is compromised.

Now turning to another embodiment in which the system provides method for recovery of registration from DRBs and single optical markers. As discussed earlier, when navigating using a surgical robotic system, continuous tracking of a DRB array that is attached to the patient is required to determine the position of any navigated instrument or tool relative to the patient's anatomy. Under certain conditions, the DRB may sometimes be partially obscured thereby making the DRB untrackable. In other situations, the DRB may be dislodged from its mounting point on the bone, also making it untrackable. When the DRB is partially obstructed, tracking or navigating must be paused and the camera system modified to restore line of sight to the markers on the DRB. When the DRB is dislodged, a new imaging scan is required and registration of the patient to the camera coordinate system is done. The present system provides a method to recover the registration or enables the continual tracking of optical makers of the surgical robot and the one or more markers mounted elsewhere on the patient.

Registration is synchronization of two coordinate systems, typically the tracking coordinate system, such as the coordinate space tracked by an optical system such as the Polaris Spectra (Northern Digital, Inc.), and the image coordinate system such as the coordinate system of a computed tomography (CT) scan. Registration is accomplished when the rigid body transformation to get from one coordinate system to the other is known. To achieve 3D registration, at least 3 reference points on a rigid body that is observed simultaneously in each coordinate system are found and the transformation of coordinates necessary to move the 3 reference points from one coordinate system to their corresponding coordinates in the other coordinate system is calculated. For example, if a tracking fixture has optical tracking markers that are in a known location (known from engineering design or located by any experimental means) in the fixture's local coordinate system and these tracking markers' xyz locations are tracked by the cameras, the transformation from camera coordinate system to fixture coordinate system can be calculated. In the field of 3D rigid body mechanics, transformations between coordinate systems are applied by multiplying each point to be transformed by a 4×4 transformation matrix. In such matrices, the first three columns describe the orientation of the rigid body and the 4th column describes the translational offset. The transformation matrix from the camera coordinate system to the fixture coordinate system may be represented as:

$$T_{Camera\text{-}Fixture}$$

And to transform a point P from the camera coordinate system to the fixture coordinate system is represented as:

$$P_{Fixture} = T_{Camera\text{-}Fixture} \times P_{camera}$$

There are provided several different methods for determining the 4×4 transformation matrix from sets of the same points in two coordinate systems. For example, the Kabsch algorithm is a method for calculating the optimal transformation matrix that minimizes the RMSD (root mean squared deviation) between two paired sets of points. Transformation matrices may be easily combined to achieve new useful transformation matrices. In one embodiment, the fixture described above may contain fiducials for detection within a CT volume. If the locations of these fiducials are known in the local coordinate system of the fixture, the transformation of coordinates from fixture to CT image coordinate system can be found as $$T_{Fixture\text{-}Image}$$

using the Kabsch or similar algorithm. As a result, the transformation results from the camera coordinate system to the coordinate system of the medical image can be determined by combining two transformations:

$$T_{Camera\text{-}Image} = T_{Camera\text{-}Fixture} \times T_{Fixture\text{-}Image}$$

If the DRB is dislodged, the relationship between fiducials and the CT are no longer the same as at the time the CT scan was taken, as a result the $T_{Fixture\text{-}Image}$ is incorrect and $T_{Camera\text{-}Image}$ is not valid.

In a preferred embodiment, a tracking array positioned on an end effector provides the location of the end effector in the coordinate system of the cameras. The robot system is equipped with encoders on each axis that precisely monitor the positions of each linkage of the robot arm. As the robot arm is moved, the position of the end effector is detected from tracking markers, but the positional change may also be calculated from kinematics by considering the geometry of each joint of the robotic arm and the amount of movement on each joint as monitored by the rotational or linear encoders. This ability to reference points in the tracking coordinate system from kinematic information provides an additional transformation calculation that can be utilized: the transformation from current tracked coordinates of the robot's end effector to a fixed reference in the camera coordinate system. That is, a frame of tracking data provides a snapshot of the tracked position of the robot end effector, but through a transformation derived from the axis encoder readings that account for the change in position due to movement of the joints, this moving frame of data can be transformed into the fixed reference frame of the robot despite any movement of the patient or camera that may occur. This transformation allows the moving array on the end effector to function the same as if another array were physically mounted to the base of the robot to track its position.

$$T_{Camera\text{-}RobotBase} = T_{Camera\text{-}EndEffector} \times T_{EndEffector\text{-}RobotBase}$$

As described in a previous embodiment a surveillance marker is used to continuously monitor the integrity of the DRB's attachment to bone. If the patient moves, both the DRB and the surveillance marker would move together without changing their relative position, but if the DRB or surveillance marker is dislodged, the relative position would change.

In another embodiment, a method for recovering the registration that is based on the last known position of the DRB relative to the robot is provided. The system continuously updates the last valid location of the DRB relative to the robot base and stores this location in system memory for later usage if necessary.

If the DRB becomes dislodged by inadvertent contact with medical personnel or equipment, the surveillance marker would show a change in offset of the DRB markers and would positively indicate that movement had occurred. If tracking data also shows that the distance between the robot's fixed reference frame and the surveillance marker on the patient have not moved, it can be safely assumed that the patient has not moved relative to the robot. As a result, the DRB may be reattached and a new registration established based on the tracked position of the robot. To establish a new registration, the new position of the DRB and robot's array would be tracked simultaneously, giving the transformation calculation from the end effector to the new DRB position. Additionally, the last known DRB location in the coordinate system of the robot would be recalled from the memory storage device. The new registration can therefore be established as:

$$T_{Camera\text{-}Image} = T_{Camera\text{-}RobotEE} \times T_{RobotEE\text{-}RobotBase} \times \\ T_{RobotBase\text{-}LastKnownDRB} \times T_{LastKnownDRB\text{-}Image}$$

With the new DRB attachment, the following is also true:

$$T_{Camera\text{-}Image} = T_{Camera\text{-}DRB} \times T_{DRB\text{-}Image}$$

Setting the two equations equal to each other, the transformation from new location of the DRB to the image can be determined as $$T_{DRB\text{-}Image} = T_{DRB\text{-}Camera} \times T_{Camera\text{-}RobotEE} \times \\ T_{RobotEE\text{-}RobotBase} \times T_{RobotBase\text{-}LastKnownDRB} \times \\ T_{LastKnownDRB\text{-}Image}$$

During collection of the new location of the DRB in the camera coordinate system, the location of the surveillance marker relative to the robot base would be continuously measured to ensure that the surveillance marker has not moved since before the DRB was dislodged. In another embodiment, if there is movement of the surveillance marker or movement of both the surveillance marker and the DRB at the time of dislodgment, a new scan and registration would be required.

In another embodiment, the system provides a method for re-registering the patient when there is a partial obstruction of the DRB to where only 2 of the 4 optical markers on the DRB remain visible while 2 optical markers are blocked. If the robot is movement when there is a partial obstruction, the motion of the robot arm is stopped until the DRB becomes fully visualized by the camera system, or if a tool or instrument is being tracked, the tool or instrument would freeze in its display on the screen. However, the system will track the DRB, if the surveillance marker remains visible. The two visible optical markers of the DRB and the surveillance marker comprise 3 points, which is the minimum points to define a rigid body. If the distances of the surveillance marker relative to the two visible points have not changed, the DRB has not moved in bone. From any previous frame of data where all markers on the DRB were visible, the transformation of the surveillance marker into the DRB coordinate system could have been determined by applying the transformation from camera to DRB to the tracked position of the surveillance marker. This value is stored to the system memory. After the optical markers on the DRB are blocked, the 2 blocked optical markers can be "reconstructed" by applying a point matching algorithm where one point set is the tracked xyz coordinates of the two DRB optical markers plus the surveillance marker and the corresponding point set to be matched is the same two DRB markers and the surveillance marker in the coordinate system of the DRB. For example, Point set 1={Visible DRB marker 1, Visible DRB marker 2, Surveillance marker}$_{DRB}$ Point set 2={Visible DRB marker 1, Visible DRB marker 2, Surveillance marker}$_{Camera}$ T$_{DRB-Camera}$ The reconstructed DRB markers are determined as this transformation applied to the known locations of the missing DRB markers in the DRB coordinate system:

$$P_{BlockedDRBmarker1,} \quad\quad\quad ^{Camera}=T_{DRB-Camera} \times P_{BlockedDRBmarker1, DRB}$$

$$P_{BlockedDRBmarker2,} \quad\quad\quad ^{Camera}=T_{DRB-Camera} \times P_{BlockedDRBmarker2, DRB}$$

Using a full set of the two previously visible DRB optical markers plus the two reconstructed markers, the normal sequence of transformations can be applied and standard tracking methods followed.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. A method of re-establishing registration without re-imaging a patient with an imaging device comprising:
    establishing registration of an image of a patient captured from the imaging device in an imaging space to a patient in a camera space based on a pose of the imaging device at the time of the image capture and a dynamic reference base (DRB) as seen by cameras of a tracking device, the DRB including a plurality of markers and adapted to be attached to the patient;
    continuously updating a last known location of markers attached to a robot as seen by the cameras of the tracking device;
    detecting a loss of registration when a distance of a surveillance marker disposed at a selected distance away from the DRB has changed;
    when the loss of registration is detected, re-establishing the registration based on the last known location of markers attached to the robot and a location of the surveillance marker as seen by the cameras of the tracking device without re-scanning the patient with the imaging device.

2. The method of claim 1, where establishing registration includes determining a transform of a pose of the image of the patient captured from the imaging device relative to the DRB as seen by the cameras (T$_{DRB-Image}$).

3. The method of claim 1, wherein re-establishing the registration includes determining a transform of a pose of the image of the patient captured from the imaging device relative to the last known DRB (T$_{LastKnownDRB-Image}$) prior to the loss of registration.

4. The method of claim 1, wherein the markers attached to the robot are attached to an end effector of the robot, and re-establishing the registration includes determining a transform between a pose of the end effector of the robot relative to the cameras of the tracking device (T$_{Camera-RobotEE}$).

5. The method of claim 1, wherein re-establishing the registration includes determining a transform between a pose of the cameras of the tracking device relative to the DRB (T$_{DRB-Camera}$) after the loss of registration.

6. The method of claim 1, wherein:
    the markers attached to the robot are attached to an end effector of the robot; and
    re-establishing the registration includes determining:
        a transform between a pose of a base of the robot relative to the end effector; and
        a transform between a pose of the last known DRB relative to the base of the robot.

7. The method of claim 1, further comprising registering the surveillance marker to the DRB.

8. The method of claim 1, wherein establishing registration includes establishing registration of a 3D image from a CT imaging device.

9. The method of claim 1, wherein the markers attached to the robot are attached to an end effector of the robot, and re-establishing the registration includes:
    determining a transform of a pose of the image of the patient captured from the imaging device relative to the last known DRB (T$_{LastKnownDRB-Image}$) prior to the loss of registration; and
    determining a transform between a pose of the end effector of the robot relative to the cameras of the tracking device (T$_{Camera-RobotEE}$).

10. The method of claim 9, wherein re-establishing the registration includes determining a transform between a pose of the cameras of the tracking device relative to the DRB (T$_{DRB-Camera}$) after the loss of registration.

11. A method of re-establishing registration without re-imaging a patient with an imaging device comprising:
    establishing registration of an image of a patient captured from the imaging device in an imaging space to a patient in a camera space based on a pose of the imaging device at the time of the image capture and a dynamic reference base (DRB) as seen by cameras of a tracking device, the DRB including a plurality of markers and adapted to be attached to the patient;
    continuously updating in a memory a last known location of markers attached to a robot as seen by the cameras of the tracking device;
    detecting a loss of registration when a distance of a surveillance marker attached to the patient at a known distance away from the DRB has changed based on the DRB and the surveillance marker as seen by the cameras of the tracking device;
    when the loss of registration is detected,
        retrieving the last known location of markers attached to the robot from the memory; and
        re-establishing the registration based on the retrieved location and a pose of the surveillance marker as seen by the cameras of the tracking device without re-scanning the patient with the imaging device.

12. The method of claim 11, where establishing registration includes determining a transform of a pose of the image of the patient captured from the imaging device relative to the DRB as seen by the cameras (T$_{DRB-Image}$).

13. The method of claim 11, wherein re-establishing the registration includes determining a transform of a pose of the image of the patient captured from the imaging device relative to the last known DRB (T$_{LastKnownDRB-Image}$) prior to the loss of registration.

14. The method of claim 11, wherein the markers attached to the robot are attached to an end effector of the robot, and re-establishing the registration includes determining a transform between a pose of the end effector of the robot relative to the cameras of the tracking device (T$_{Camera-RobotEE}$).

15. The method of claim 11, wherein re-establishing the registration includes determining a transform between a pose of the cameras of the tracking device relative to the DRB (T$_{DRB-Camera}$) after the loss of registration.

16. The method of claim 11, wherein:
the markers attached to the robot are attached to an end effector of the robot; and
re-establishing the registration includes determining:
  a transform between a pose of a base of the robot relative to the end effector; and
  a transform between a pose of the last known DRB relative to the base of the robot.

17. The method of claim 11, further comprising registering the surveillance marker to the DRB.

18. The method of claim 11, wherein establishing registration includes establishing registration of a 3D image from a CT imaging device.

19. The method of claim 11, wherein the markers attached to the robot are attached to an end effector of the robot, and re-establishing the registration includes:
  determining a transform of a pose of the image of the patient captured from the imaging device relative to the last known DRB ($T_{LastKnownDRB-Image}$) prior to the loss of registration; and
  determining a transform between a pose of the end effector of the robot relative to the cameras of the tracking device ($T_{Camera-RobotEE}$).

20. The method of claim 19, wherein re-establishing the registration includes determining a transform between a pose of the cameras of the tracking device relative to the DRB ($T_{DRB-Camera}$) after the loss of registration.

* * * * *